United States Patent
Cho et al.

(10) Patent No.: US 10,319,649 B2
(45) Date of Patent: Jun. 11, 2019

(54) OPTICAL EMISSION SPECTROSCOPY (OES) FOR REMOTE PLASMA MONITORING

(71) Applicant: Applied Materials, Inc., Santa Clara, CA (US)

(72) Inventors: Tae Seung Cho, San Jose, CA (US); Soonam Park, Sunnyvale, CA (US); Junghoon Kim, Santa Clara, CA (US); Dmitry Lubomirsky, Cupertino, CA (US); Shankar Venkataraman, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/484,985

(22) Filed: Apr. 11, 2017

(65) Prior Publication Data

US 2018/0294198 A1 Oct. 11, 2018

(51) Int. Cl.
*H01L 21/26* (2006.01)
*H01L 21/66* (2006.01)
(Continued)

(52) U.S. Cl.
CPC .......... *H01L 22/26* (2013.01); *G01N 21/73* (2013.01); *H01J 37/32568* (2013.01);
(Continued)

(58) Field of Classification Search
CPC .............. H01L 22/26; H01L 21/3065; H01L 21/67069; H01L 21/67253; G01N 21/73; H01J 37/32568; H01J 37/32743
See application file for complete search history.

(56) References Cited

U.S. PATENT DOCUMENTS

| 2,369,620 A | 2/1945 | Sullivan et al. |
| 3,401,302 A | 9/1968 | Thorpe |

(Continued)

FOREIGN PATENT DOCUMENTS

| CN | 1124364 A | 6/1996 |
| CN | 1847450 A | 10/2006 |

(Continued)

OTHER PUBLICATIONS

Won et al. Derwent 2006-065772; Sep. 7, 2014, 10 pages.
(Continued)

*Primary Examiner* — Duy Vu N Deo
(74) *Attorney, Agent, or Firm* — Kilpatrick Townsend & Stockton LLP

(57) ABSTRACT

Methods and systems for etching substrates using a remote plasma are described. Remotely excited etchants are formed in a remote plasma and flowed through a showerhead into a substrate processing region to etch the substrate. Optical emission spectra are acquired from the substrate processing region just above the substrate. The optical emission spectra may be used to determine an endpoint of the etch, determine the etch rate or otherwise characterize the etch process. A weak plasma may be present in the substrate processing region. The weak plasma may have much lower intensity than the remote plasma. In cases where no bias plasma is used above the substrate in an etch process, a weak plasma may be ignited near a viewport disposed near the side of the substrate processing region to characterize the etchants.

18 Claims, 9 Drawing Sheets

(51) Int. Cl.
*G01N 21/73* (2006.01)
*H01L 21/67* (2006.01)
*H01J 37/32* (2006.01)
*H01L 21/311* (2006.01)

(52) U.S. Cl.
CPC .. *H01J 37/32743* (2013.01); *H01L 21/31116* (2013.01); *H01L 21/67253* (2013.01); *G01N 2201/08* (2013.01); *G01N 2201/0833* (2013.01); *H01J 37/32082* (2013.01); *H01J 2237/3341* (2013.01)

(56) References Cited

U.S. PATENT DOCUMENTS

| | | |
|---|---|---|
| 3,451,840 A | 6/1969 | Hough |
| 3,537,474 A | 11/1970 | Rohrer |
| 3,756,511 A | 9/1973 | Shinroku |
| 3,937,857 A | 2/1976 | Brummett et al. |
| 3,969,077 A | 7/1976 | Hill |
| 4,006,047 A | 2/1977 | Brummett et al. |
| 4,190,488 A | 2/1980 | Winters |
| 4,209,357 A | 6/1980 | Gorin et al. |
| 4,214,946 A | 7/1980 | Forget et al. |
| 4,232,060 A | 11/1980 | Mallory, Jr. |
| 4,234,628 A | 11/1980 | DuRose |
| 4,265,943 A | 5/1981 | Goldstein et al. |
| 4,340,462 A | 7/1982 | Koch |
| 4,341,592 A | 7/1982 | Shortes et al. |
| 4,361,418 A | 11/1982 | Tscheppe |
| 4,361,441 A | 11/1982 | Tylko |
| 4,364,803 A | 12/1982 | Nidola et al. |
| 4,368,223 A | 1/1983 | Kobayashi et al. |
| 4,374,698 A | 2/1983 | Sanders et al. |
| 4,397,812 A | 8/1983 | Mallory, Jr. |
| 4,468,413 A | 8/1984 | Bachmann |
| 4,565,601 A | 1/1986 | Kakehi et al. |
| 4,579,618 A | 4/1986 | Celestino et al. |
| 4,585,920 A | 4/1986 | Hoog et al. |
| 4,610,775 A | 9/1986 | Phifer |
| 4,625,678 A | 12/1986 | Shloya et al. |
| 4,632,857 A | 12/1986 | Mallory, Jr. |
| 4,656,052 A | 4/1987 | Satou et al. |
| 4,656,076 A | 4/1987 | Vetanen et al. |
| 4,668,335 A | 5/1987 | Mockler |
| 4,690,746 A | 9/1987 | McInerney et al. |
| 4,715,937 A | 12/1987 | Moslehi et al. |
| 4,749,440 A | 6/1988 | Blackwood et al. |
| 4,753,898 A | 6/1988 | Parrillo et al. |
| 4,786,360 A | 11/1988 | Cote et al. |
| 4,792,378 A | 12/1988 | Rose et al. |
| 4,793,897 A | 12/1988 | Dunfield et al. |
| 4,807,016 A | 2/1989 | Douglas |
| 4,810,520 A | 3/1989 | Wu |
| 4,816,638 A | 3/1989 | Ukai et al. |
| 4,820,377 A | 4/1989 | Davis et al. |
| 4,828,649 A | 5/1989 | Davis |
| 4,857,140 A | 8/1989 | Loewenstein |
| 4,867,841 A | 9/1989 | Loewenstein et al. |
| 4,904,621 A | 2/1990 | Lowenstein et al. |
| 4,913,929 A | 4/1990 | Moslehi et al. |
| 4,919,750 A | 4/1990 | Bausmith et al. |
| 4,946,903 A | 8/1990 | Gardella et al. |
| 4,951,601 A | 8/1990 | Maydan et al. |
| 4,960,488 A | 10/1990 | Law et al. |
| 4,980,018 A | 12/1990 | Mu et al. |
| 4,981,551 A | 1/1991 | Palmour |
| 4,985,372 A | 1/1991 | Narita et al. |
| 4,991,542 A | 2/1991 | Kohmura et al. |
| 4,992,136 A | 2/1991 | Tachi et al. |
| 4,993,358 A | 2/1991 | Mahawili |
| 4,994,404 A | 2/1991 | Sheng et al. |
| 5,000,113 A | 3/1991 | Wang et al. |
| 5,006,192 A | 4/1991 | Deguchi |
| 5,010,842 A | 4/1991 | Oda et al. |
| 5,013,691 A | 5/1991 | Lory et al. |
| 5,028,565 A | 7/1991 | Chang |
| 5,030,319 A | 7/1991 | Nishino et al. |
| 5,038,713 A | 8/1991 | Kawakami et al. |
| 5,045,244 A | 9/1991 | Marlett |
| 5,061,838 A | 10/1991 | Lane et al. |
| 5,069,938 A | 12/1991 | Lorimer et al. |
| 5,083,030 A | 1/1992 | Stavov |
| 5,089,441 A | 2/1992 | Moslehi |
| 5,089,442 A | 2/1992 | Olmer |
| 5,147,692 A | 9/1992 | Bengston |
| 5,156,881 A | 10/1992 | Okano et al. |
| 5,180,435 A | 1/1993 | Markunas et al. |
| 5,186,718 A | 2/1993 | Tepman et al. |
| 5,188,706 A | 2/1993 | Hori et al. |
| 5,198,034 A | 3/1993 | deBoer et al. |
| 5,200,016 A | 4/1993 | Namose |
| 5,203,911 A | 4/1993 | Sricharoenchalkit et al. |
| 5,215,787 A | 6/1993 | Homma |
| 5,221,427 A | 6/1993 | Koinuma et al. |
| 5,228,501 A | 7/1993 | Tepman et al. |
| 5,231,690 A | 7/1993 | Soma et al. |
| 5,235,139 A | 8/1993 | Bengston et al. |
| 5,238,499 A | 8/1993 | van de Ven et al. |
| 5,240,497 A | 8/1993 | Shacham et al. |
| 5,248,371 A | 9/1993 | Maher et al. |
| 5,248,527 A | 9/1993 | Uchida et al. |
| 5,252,178 A | 10/1993 | Moslehi |
| 5,266,157 A | 11/1993 | Kadomura |
| 5,269,881 A | 12/1993 | Sekiya |
| 5,270,125 A | 12/1993 | America et al. |
| 5,271,972 A | 12/1993 | Kwok et al. |
| 5,275,977 A | 1/1994 | Otsubo et al. |
| 5,277,750 A | 1/1994 | Wolgang |
| 5,279,669 A | 1/1994 | Lee |
| 5,279,865 A | 1/1994 | Chebi et al. |
| 5,288,518 A | 2/1994 | Homma |
| 5,290,382 A | 3/1994 | Zarowin et al. |
| 5,290,383 A * | 3/1994 | Koshimizu ....... H01J 37/32935 156/345.25 |
| 5,292,370 A | 3/1994 | Tsai et al. |
| 5,292,682 A | 3/1994 | Stevens et al. |
| 5,300,463 A | 4/1994 | Cathey et al. |
| 5,302,233 A | 4/1994 | Kim et al. |
| 5,304,250 A | 4/1994 | Sameshima et al. |
| 5,306,530 A | 4/1994 | Strongin et al. |
| 5,314,724 A | 5/1994 | Tsukune et al. |
| 5,319,247 A | 6/1994 | Matsuura |
| 5,326,427 A | 7/1994 | Jerbic |
| 5,328,558 A | 7/1994 | Kawamura et al. |
| 5,328,810 A | 7/1994 | Lowrey et al. |
| 5,330,578 A | 7/1994 | Sakama |
| 5,334,552 A | 8/1994 | Homma |
| 5,345,999 A | 9/1994 | Hosokawa |
| 5,352,636 A | 10/1994 | Beinglass |
| 5,356,478 A | 10/1994 | Chen et al. |
| 5,362,526 A | 11/1994 | Wang et al. |
| 5,366,585 A | 11/1994 | Robertson et al. |
| 5,368,897 A | 11/1994 | Kurihara et al. |
| 5,378,316 A | 1/1995 | Franke et al. |
| 5,380,560 A | 1/1995 | Kaja et al. |
| 5,382,311 A | 1/1995 | Ishikawa et al. |
| 5,384,284 A | 1/1995 | Doan et al. |
| 5,385,763 A | 1/1995 | Okano et al. |
| 5,399,237 A | 3/1995 | Keswick et al. |
| 5,399,529 A | 3/1995 | Homma |
| 5,403,434 A | 4/1995 | Moslehi |
| 5,413,670 A | 5/1995 | Langan et al. |
| 5,413,967 A | 5/1995 | Matsuda et al. |
| 5,415,890 A | 5/1995 | Kloiber et al. |
| 5,416,048 A | 5/1995 | Blalock et al. |
| 5,420,075 A | 5/1995 | Homma et al. |
| 5,429,995 A | 7/1995 | Nishiyama et al. |
| 5,439,553 A | 8/1995 | Grant et al. |
| 5,451,259 A | 9/1995 | Krogh |
| 5,464,499 A | 11/1995 | Moslehi |
| 5,468,342 A | 11/1995 | Nulty et al. |
| 5,474,589 A | 12/1995 | Ohga et al. |
| 5,478,403 A | 12/1995 | Shinigawa et al. |
| 5,478,462 A | 12/1995 | Walsh |

(56) References Cited

U.S. PATENT DOCUMENTS

| | | |
|---|---|---|
| 5,483,920 A | 1/1996 | Pryor |
| 5,494,494 A | 2/1996 | Mizuno et al. |
| 5,500,249 A | 3/1996 | Telford et al. |
| 5,505,816 A | 4/1996 | Barnes et al. |
| 5,510,216 A | 4/1996 | Calabrese et al. |
| 5,516,367 A | 5/1996 | Lei et al. |
| 5,518,962 A | 5/1996 | Murao |
| 5,531,835 A | 7/1996 | Fodor et al. |
| 5,534,070 A | 7/1996 | Okamura et al. |
| 5,536,360 A | 7/1996 | Nguyen et al. |
| 5,549,780 A | 8/1996 | Koinuma et al. |
| 5,558,717 A | 9/1996 | Zhao et al. |
| 5,560,779 A | 10/1996 | Knowles et al. |
| 5,563,105 A | 10/1996 | Dobuzinsky et al. |
| 5,567,243 A | 10/1996 | Foster et al. |
| 5,571,576 A | 11/1996 | Qian et al. |
| 5,575,853 A | 11/1996 | Arami et al. |
| 5,578,130 A | 11/1996 | Hayashi et al. |
| 5,578,161 A | 11/1996 | Auda |
| 5,580,421 A | 12/1996 | Hiatt et al. |
| 5,591,269 A | 1/1997 | Arami et al. |
| 5,592,358 A | 1/1997 | Shamouilian |
| 5,599,740 A | 2/1997 | Jang et al. |
| 5,614,055 A | 3/1997 | Fairbairn et al. |
| 5,616,518 A | 4/1997 | Foo et al. |
| 5,624,582 A | 4/1997 | Cain |
| 5,626,922 A | 5/1997 | Miyanaga et al. |
| 5,628,829 A | 5/1997 | Foster et al. |
| 5,635,086 A | 6/1997 | Warren, Jr. |
| 5,645,645 A | 7/1997 | Zhang et al. |
| 5,648,125 A | 7/1997 | Cane |
| 5,648,175 A | 7/1997 | Russell et al. |
| 5,656,093 A | 8/1997 | Burkhart et al. |
| 5,660,957 A | 8/1997 | Chou et al. |
| 5,661,093 A | 8/1997 | Ravi et al. |
| 5,670,066 A | 9/1997 | Barnes et al. |
| 5,674,787 A | 10/1997 | Zhao et al. |
| 5,676,758 A | 10/1997 | Hasgawa et al. |
| 5,679,606 A | 10/1997 | Wang et al. |
| 5,685,946 A | 11/1997 | Fathauer et al. |
| 5,688,331 A | 11/1997 | Aruga et al. |
| 5,695,810 A | 12/1997 | Dubin et al. |
| 5,712,185 A | 1/1998 | Tsai et al. |
| 5,716,500 A | 2/1998 | Bardos et al. |
| 5,716,506 A | 2/1998 | Maclay et al. |
| 5,719,085 A | 2/1998 | Moon et al. |
| 5,733,816 A | 3/1998 | Iyer et al. |
| 5,747,373 A | 5/1998 | Yu |
| 5,753,886 A | 5/1998 | Iwamura et al. |
| 5,755,859 A | 5/1998 | Brusic et al. |
| 5,756,400 A | 5/1998 | Ye et al. |
| 5,756,402 A | 5/1998 | Jimbo et al. |
| 5,772,770 A | 6/1998 | Suda et al. |
| 5,781,693 A | 7/1998 | Ballance et al. |
| 5,786,276 A | 7/1998 | Brooks et al. |
| 5,788,825 A | 8/1998 | Park et al. |
| 5,789,300 A | 8/1998 | Fulford |
| 5,792,376 A | 8/1998 | Kanai et al. |
| 5,800,686 A | 9/1998 | Littau et al. |
| 5,804,259 A | 9/1998 | Robles |
| 5,812,403 A | 9/1998 | Fong et al. |
| 5,814,238 A | 9/1998 | Ashby et al. |
| 5,814,365 A | 9/1998 | Mahawill |
| 5,820,723 A | 10/1998 | Benjamin et al. |
| 5,824,599 A | 10/1998 | Schacham-Diamand et al. |
| 5,830,805 A | 11/1998 | Schacham-Diamand et al. |
| 5,835,334 A | 11/1998 | McMillin et al. |
| 5,843,538 A | 12/1998 | Ehrsam et al. |
| 5,843,847 A | 12/1998 | Pu et al. |
| 5,844,195 A | 12/1998 | Fairbairn et al. |
| 5,846,332 A | 12/1998 | Zhao et al. |
| 5,846,373 A | 12/1998 | Pirkle et al. |
| 5,846,375 A | 12/1998 | Gilchrist et al. |
| 5,846,598 A | 12/1998 | Semkow et al. |
| 5,849,639 A | 12/1998 | Molloy et al. |
| 5,850,105 A | 12/1998 | Dawson et al. |
| 5,855,681 A | 1/1999 | Maydan et al. |
| 5,855,685 A | 1/1999 | Tobe et al. |
| 5,856,240 A | 1/1999 | Sinha et al. |
| 5,858,876 A | 1/1999 | Chew |
| 5,863,376 A | 1/1999 | Wicker |
| 5,865,896 A | 2/1999 | Nowak |
| 5,866,483 A | 2/1999 | Shiau et al. |
| 5,872,052 A | 2/1999 | Iyer |
| 5,872,058 A | 2/1999 | Van Cleemput et al. |
| 5,882,424 A | 3/1999 | Taylor et al. |
| 5,882,786 A | 3/1999 | Nassau et al. |
| 5,883,012 A | 3/1999 | Chiou |
| 5,885,404 A | 3/1999 | Kim et al. |
| 5,885,749 A | 3/1999 | Huggins et al. |
| 5,888,906 A | 3/1999 | Sandhu et al. |
| 5,891,349 A | 4/1999 | Tobe et al. |
| 5,891,513 A | 4/1999 | Dubin et al. |
| 5,897,751 A | 4/1999 | Makowiecki |
| 5,899,752 A | 5/1999 | Hey et al. |
| 5,900,163 A | 5/1999 | Yi et al. |
| 5,904,827 A | 5/1999 | Reynolds |
| 5,907,790 A | 5/1999 | Kellam |
| 5,910,340 A | 6/1999 | Uchida et al. |
| 5,913,147 A | 6/1999 | Dubin et al. |
| 5,913,978 A | 6/1999 | Kato et al. |
| 5,915,190 A | 6/1999 | Pirkle |
| 5,918,116 A | 6/1999 | Chittipeddi |
| 5,919,332 A | 7/1999 | Koshiishi et al. |
| 5,920,792 A | 7/1999 | Lin |
| 5,926,737 A | 7/1999 | Ameen et al. |
| 5,932,077 A | 8/1999 | Reynolds |
| 5,933,757 A | 8/1999 | Yoshikawa et al. |
| 5,935,334 A | 8/1999 | Fong et al. |
| 5,935,340 A | 8/1999 | Xia et al. |
| 5,937,323 A | 8/1999 | Orczyk et al. |
| 5,939,831 A | 8/1999 | Fong et al. |
| 5,942,075 A | 8/1999 | Nagahata et al. |
| 5,944,049 A | 8/1999 | Beyer et al. |
| 5,944,902 A | 8/1999 | Redeker et al. |
| 5,948,702 A | 9/1999 | Rotondaro |
| 5,951,601 A | 9/1999 | Lesinski et al. |
| 5,951,776 A | 9/1999 | Selyutin et al. |
| 5,951,896 A | 9/1999 | Mahawill |
| 5,953,591 A | 9/1999 | Ishihara et al. |
| 5,953,635 A | 9/1999 | Andideh |
| 5,963,840 A | 10/1999 | Xia et al. |
| 5,968,587 A | 10/1999 | Frankel et al. |
| 5,968,610 A | 10/1999 | Liu et al. |
| 5,969,422 A | 10/1999 | Ting et al. |
| 5,976,327 A | 11/1999 | Tanaka |
| 5,990,000 A | 11/1999 | Hong et al. |
| 5,990,013 A | 11/1999 | Berenguer et al. |
| 5,993,916 A | 11/1999 | Zhao et al. |
| 5,994,209 A | 11/1999 | Yieh et al. |
| 5,997,649 A | 12/1999 | Hillman |
| 5,997,962 A | 12/1999 | Ogasawara et al. |
| 6,004,884 A | 12/1999 | Abraham |
| 6,007,635 A | 12/1999 | Mahawill |
| 6,007,785 A | 12/1999 | Liou |
| 6,010,962 A | 1/2000 | Liu et al. |
| 6,013,191 A | 1/2000 | Nasser-Faili et al. |
| 6,013,584 A | 1/2000 | M'Saad |
| 6,015,724 A | 1/2000 | Yamazaki et al. |
| 6,015,747 A | 1/2000 | Lopatin et al. |
| 6,017,414 A | 1/2000 | Koemtzopoulos et al. |
| 6,019,848 A | 2/2000 | Kiyama et al. |
| 6,020,271 A | 2/2000 | Yanagida |
| 6,030,666 A | 2/2000 | Lam et al. |
| 6,030,881 A | 2/2000 | Papasouliotis et al. |
| 6,035,101 A | 3/2000 | Sajoto et al. |
| 6,036,878 A | 3/2000 | Collins et al. |
| 6,037,018 A | 3/2000 | Jang et al. |
| 6,037,266 A | 3/2000 | Tao et al. |
| 6,039,834 A | 3/2000 | Tanaka et al. |
| 6,039,851 A | 3/2000 | Iyer |
| 6,053,982 A | 4/2000 | Halpin et al. |
| 6,059,643 A | 5/2000 | Hu et al. |
| 6,063,683 A | 5/2000 | Wu et al. |

(56) References Cited

U.S. PATENT DOCUMENTS

| | | |
|---|---|---|
| 6,063,712 A | 5/2000 | Gilton et al. |
| 6,065,424 A | 5/2000 | Shacham-Diamand et al. |
| 6,065,425 A | 5/2000 | Takaki et al. |
| 6,072,147 A | 6/2000 | Koshiishi |
| 6,072,227 A | 6/2000 | Yau et al. |
| 6,074,512 A | 6/2000 | Collins et al. |
| 6,074,514 A | 6/2000 | Bjorkman et al. |
| 6,077,384 A | 6/2000 | Collins et al. |
| 6,077,780 A | 6/2000 | Dubin |
| 6,079,356 A | 6/2000 | Umotoy et al. |
| 6,080,529 A | 6/2000 | Ye et al. |
| 6,081,414 A | 6/2000 | Flanigan et al. |
| 6,083,344 A | 7/2000 | Hanawa et al. |
| 6,083,844 A | 7/2000 | Bui-Le et al. |
| 6,086,677 A | 7/2000 | Umotoy et al. |
| 6,087,278 A | 7/2000 | Kim et al. |
| 6,090,212 A | 7/2000 | Mahawill |
| 6,093,457 A | 7/2000 | Okumura |
| 6,093,594 A | 7/2000 | Yeap et al. |
| 6,099,697 A | 8/2000 | Hausmann |
| 6,107,199 A | 8/2000 | Allen et al. |
| 6,110,530 A | 8/2000 | Chen et al. |
| 6,110,832 A | 8/2000 | Morgan et al. |
| 6,110,836 A | 8/2000 | Cohen et al. |
| 6,110,838 A | 8/2000 | Loewenstein |
| 6,113,771 A | 9/2000 | Landau et al. |
| 6,114,216 A | 9/2000 | Yieh et al. |
| 6,117,245 A | 9/2000 | Mandrekar et al. |
| 6,120,640 A | 9/2000 | Shih et al. |
| 6,136,163 A | 10/2000 | Cheung et al. |
| 6,136,165 A | 10/2000 | Moslehi et al. |
| 6,136,685 A | 10/2000 | Narwankar et al. |
| 6,136,693 A | 10/2000 | Chan et al. |
| 6,140,234 A | 10/2000 | Uzoh et al. |
| 6,144,099 A | 11/2000 | Lopatin et al. |
| 6,147,009 A | 11/2000 | Grill et al. |
| 6,148,761 A | 11/2000 | Majewski et al. |
| 6,149,828 A | 11/2000 | Vaartstra |
| 6,150,628 A | 11/2000 | Smith et al. |
| 6,153,935 A | 11/2000 | Edelstein et al. |
| 6,161,500 A | 12/2000 | Kopacz et al. |
| 6,161,576 A | 12/2000 | Maher et al. |
| 6,162,302 A | 12/2000 | Raghavan et al. |
| 6,162,370 A | 12/2000 | Hackett et al. |
| 6,165,912 A | 12/2000 | McConnell et al. |
| 6,167,834 B1 | 1/2001 | Wang et al. |
| 6,169,021 B1 | 1/2001 | Akram et al. |
| 6,170,428 B1 | 1/2001 | Redeker et al. |
| 6,171,661 B1 | 1/2001 | Zheng et al. |
| 6,174,450 B1 | 1/2001 | Patrick et al. |
| 6,174,810 B1 | 1/2001 | Patrick et al. |
| 6,174,812 B1 | 1/2001 | Hsuing et al. |
| 6,176,198 B1 | 1/2001 | Kao et al. |
| 6,176,667 B1 | 1/2001 | Fairbairn |
| 6,177,245 B1 | 1/2001 | Ward et al. |
| 6,179,924 B1 | 1/2001 | Zhao et al. |
| 6,180,523 B1 | 1/2001 | Lee et al. |
| 6,182,602 B1 | 2/2001 | Redeker et al. |
| 6,182,603 B1 | 2/2001 | Shang et al. |
| 6,184,121 B1 | 2/2001 | Buchwalter et al. |
| 6,186,091 B1 | 2/2001 | Chu et al. |
| 6,189,483 B1 | 2/2001 | Ishikawa et al. |
| 6,190,233 B1 | 2/2001 | Hong et al. |
| 6,194,038 B1 | 2/2001 | Rossman |
| 6,197,181 B1 | 3/2001 | Chen |
| 6,197,364 B1 | 3/2001 | Paunovic et al. |
| 6,197,680 B1 | 3/2001 | Lin et al. |
| 6,197,688 B1 | 3/2001 | Simpson |
| 6,197,705 B1 | 3/2001 | Vassiliev |
| 6,198,616 B1 | 3/2001 | Dahimene et al. |
| 6,203,863 B1 | 3/2001 | Liu et al. |
| 6,204,200 B1 | 3/2001 | Shieh et al. |
| 6,210,486 B1 | 4/2001 | Mizukami et al. |
| 6,217,658 B1 | 4/2001 | Orczyk et al. |
| 6,220,201 B1 | 4/2001 | Nowak |
| 6,225,745 B1 | 5/2001 | Srivastava |
| 6,228,233 B1 | 5/2001 | Lakshmikanthan et al. |
| 6,228,751 B1 | 5/2001 | Yamazaki et al. |
| 6,228,758 B1 | 5/2001 | Pellerin et al. |
| 6,235,643 B1 | 5/2001 | Mui et al. |
| 6,237,527 B1 | 5/2001 | Kellerman et al. |
| 6,238,513 B1 | 5/2001 | Arnold et al. |
| 6,238,582 B1 | 5/2001 | Williams et al. |
| 6,197,151 B1 | 6/2001 | Kaji et al. |
| 6,241,845 B1 | 6/2001 | Gadgil et al. |
| 6,242,349 B1 | 6/2001 | Nogami et al. |
| 6,244,211 B1 | 6/2001 | Nishikawa et al. |
| 6,245,396 B1 | 6/2001 | Nogami |
| 6,245,670 B1 | 6/2001 | Cheung et al. |
| 6,251,236 B1 | 6/2001 | Stevens |
| 6,251,802 B1 | 6/2001 | Moore et al. |
| 6,258,170 B1 | 7/2001 | Somekh et al. |
| 6,258,220 B1 | 7/2001 | Dordi et al. |
| 6,258,223 B1 | 7/2001 | Cheung et al. |
| 6,258,270 B1 | 7/2001 | Hilgendorff et al. |
| 6,261,637 B1 | 7/2001 | Oberle |
| 6,277,733 B1 | 8/2001 | Smith |
| 6,277,752 B1 | 8/2001 | Chen |
| 6,277,763 B1 | 8/2001 | Kugimiya et al. |
| 6,281,072 B1 | 8/2001 | Li et al. |
| 6,281,135 B1 | 8/2001 | Han et al. |
| 6,284,146 B1 | 9/2001 | Kim et al. |
| 6,291,282 B1 | 9/2001 | Wilk et al. |
| 6,291,348 B1 | 9/2001 | Lopatin et al. |
| 6,302,964 B1 | 10/2001 | Umotoy et al. |
| 6,303,044 B1 | 10/2001 | Koemtzopoulos |
| 6,303,418 B1 | 10/2001 | Cha et al. |
| 6,306,772 B1 | 10/2001 | Lin |
| 6,308,654 B1 | 10/2001 | Schneider et al. |
| 6,308,776 B1 | 10/2001 | Sloan |
| 6,310,755 B1 | 10/2001 | Busato et al. |
| 6,312,554 B1 | 11/2001 | Ye |
| 6,312,995 B1 | 11/2001 | Yu |
| 6,319,387 B1 | 11/2001 | Krishnamoorthy et al. |
| 6,321,587 B1 | 11/2001 | Laush |
| 6,322,716 B1 | 11/2001 | Qiao et al. |
| 6,323,128 B1 | 11/2001 | Sambucetti et al. |
| 6,335,288 B1 | 1/2002 | Kwan et al. |
| 6,340,435 B1 | 1/2002 | Bjorkman et al. |
| 6,342,733 B1 | 1/2002 | Hu et al. |
| RE37,546 E | 2/2002 | Mahawili |
| 6,344,410 B1 | 2/2002 | Lopatin et al. |
| 6,348,407 B1 | 2/2002 | Gupta et al. |
| 6,350,320 B1 | 2/2002 | Sherstinsky et al. |
| 6,350,697 B1 | 2/2002 | Richardson |
| 6,351,013 B1 | 2/2002 | Luning et al. |
| 6,352,081 B1 | 3/2002 | Lu et al. |
| 6,355,573 B1 | 3/2002 | Okumura |
| 6,364,949 B1 | 4/2002 | Or et al. |
| 6,364,954 B2 | 4/2002 | Umotoy et al. |
| 6,364,957 B1 | 4/2002 | Schneider et al. |
| 6,375,748 B1 | 4/2002 | Yudovsky et al. |
| 6,376,386 B1 | 4/2002 | Oshima |
| 6,379,575 B1 | 4/2002 | Yin et al. |
| 6,383,896 B1 | 5/2002 | Kirimura et al. |
| 6,383,951 B1 | 5/2002 | Li |
| 6,387,207 B1 | 5/2002 | Janakiraman et al. |
| 6,391,753 B1 | 5/2002 | Yu |
| 6,395,150 B1 | 5/2002 | Van Cleemput et al. |
| 6,403,491 B1 | 6/2002 | Liu et al. |
| 6,415,736 B1 | 7/2002 | Hao et al. |
| 6,416,647 B1 | 7/2002 | Dordi et al. |
| 6,418,874 B1 | 7/2002 | Cox et al. |
| 6,423,284 B1 | 7/2002 | Arno |
| 6,427,623 B2 | 8/2002 | Ko |
| 6,429,465 B1 | 8/2002 | Yagi et al. |
| 6,432,819 B1 | 8/2002 | Pavate et al. |
| 6,432,831 B2 | 8/2002 | Dhindsa et al. |
| 6,436,193 B1 | 8/2002 | Kasai et al. |
| 6,436,816 B1 | 8/2002 | Lee et al. |
| 6,440,863 B1 | 8/2002 | Tsai et al. |
| 6,441,492 B1 | 8/2002 | Cunningham |
| 6,446,572 B1 | 9/2002 | Brcka |
| 6,448,537 B1 | 9/2002 | Nering |

(56) References Cited

U.S. PATENT DOCUMENTS

| | | |
|---|---|---|
| 6,458,718 B1 | 10/2002 | Todd |
| 6,461,974 B1 | 10/2002 | Ni et al. |
| 6,462,371 B1 | 10/2002 | Weimer et al. |
| 6,462,372 B1 | 10/2002 | Xia et al. |
| 6,465,051 B1 | 10/2002 | Sahin et al. |
| 6,465,350 B1 | 10/2002 | Taylor et al. |
| 6,465,366 B1 | 10/2002 | Nemani et al. |
| 6,477,980 B1 | 11/2002 | White et al. |
| 6,479,373 B2 | 11/2002 | Dreybrodt et al. |
| 6,488,984 B1 | 12/2002 | Wada et al. |
| 6,494,959 B1 | 12/2002 | Samoilov et al. |
| 6,499,425 B1 | 12/2002 | Sandhu et al. |
| 6,500,728 B1 | 12/2002 | Wang |
| 6,503,843 B1 | 1/2003 | Xia et al. |
| 6,506,291 B2 | 1/2003 | Tsai et al. |
| 6,509,283 B1 | 1/2003 | Thomas |
| 6,509,623 B2 | 1/2003 | Zhao |
| 6,516,815 B1 | 2/2003 | Stevens et al. |
| 6,518,548 B2 | 2/2003 | Sugaya et al. |
| 6,527,968 B1 | 3/2003 | Wang et al. |
| 6,528,409 B1 | 3/2003 | Lopatin et al. |
| 6,528,751 B1 | 3/2003 | Hoffman et al. |
| 6,537,707 B1 | 3/2003 | Lee |
| 6,537,733 B2 | 3/2003 | Campana et al. |
| 6,541,397 B1 | 4/2003 | Bencher |
| 6,541,671 B1 | 4/2003 | Martinez et al. |
| 6,544,340 B2 | 4/2003 | Yudovsky |
| 6,547,977 B1 | 4/2003 | Yan et al. |
| 6,551,924 B1 | 4/2003 | Dalton et al. |
| 6,558,564 B1 | 5/2003 | Loewenhardt |
| 6,565,661 B1 | 5/2003 | Nguyen |
| 6,565,729 B2 | 5/2003 | Chen et al. |
| 6,569,773 B1 | 5/2003 | Gellrich et al. |
| 6,572,937 B2 | 6/2003 | Hakovirta et al. |
| 6,573,030 B1 | 6/2003 | Fairbairn et al. |
| 6,573,606 B2 | 6/2003 | Sambucetti et al. |
| 6,585,851 B1 | 7/2003 | Ohmi et al. |
| 6,586,163 B1 | 7/2003 | Okabe et al. |
| 6,596,599 B1 | 7/2003 | Guo |
| 6,596,654 B1 | 7/2003 | Bayman et al. |
| 6,602,434 B1 | 8/2003 | Hung et al. |
| 6,602,806 B1 | 8/2003 | Xia et al. |
| 6,603,269 B1 | 8/2003 | Vo et al. |
| 6,605,874 B2 | 8/2003 | Leu et al. |
| 6,616,967 B1 | 9/2003 | Test |
| 6,627,532 B1 | 9/2003 | Gaillard et al. |
| 6,635,575 B1 | 10/2003 | Xia et al. |
| 6,635,578 B1 | 10/2003 | Xu et al. |
| 6,638,810 B2 | 10/2003 | Bakli et al. |
| 6,645,301 B2 | 11/2003 | Sainty et al. |
| 6,645,550 B1 | 11/2003 | Cheung et al. |
| 6,656,831 B1 | 12/2003 | Lee et al. |
| 6,656,837 B2 | 12/2003 | Xu et al. |
| 6,656,848 B1 | 12/2003 | Scanlan et al. |
| 6,663,715 B1 | 12/2003 | Yuda et al. |
| 6,677,242 B1 | 1/2004 | Liu et al. |
| 6,679,981 B1 | 1/2004 | Pan et al. |
| 6,688,375 B1 | 2/2004 | Turner |
| 6,713,356 B1 | 3/2004 | Skotnicki et al. |
| 6,713,835 B1 | 3/2004 | Horak et al. |
| 6,717,189 B2 | 4/2004 | Inoue et al. |
| 6,720,213 B1 | 4/2004 | Gambino et al. |
| 6,736,147 B2 | 5/2004 | Satoh et al. |
| 6,736,987 B1 | 5/2004 | Cho |
| 6,740,247 B1 | 5/2004 | Han et al. |
| 6,740,585 B2 | 5/2004 | Yoon et al. |
| 6,740,977 B2 | 5/2004 | Ahn et al. |
| 6,743,473 B1 | 6/2004 | Parkhe et al. |
| 6,743,732 B1 | 6/2004 | Lin et al. |
| 6,756,235 B1 | 6/2004 | Liu et al. |
| 6,759,261 B2 | 7/2004 | Shimokohbe et al. |
| 6,762,127 B2 | 7/2004 | Boiteux et al. |
| 6,762,435 B2 | 7/2004 | Towle |
| 6,764,958 B1 | 7/2004 | Nemani et al. |
| 6,765,273 B1 | 7/2004 | Chau et al. |
| 6,767,834 B2 | 7/2004 | Chung et al. |
| 6,768,079 B2 | 7/2004 | Kosakai |
| 6,770,166 B1 | 8/2004 | Fisher |
| 6,772,827 B2 | 8/2004 | Keller et al. |
| 6,792,889 B2 | 9/2004 | Nakano et al. |
| 6,794,290 B1 | 9/2004 | Papasouliotis et al. |
| 6,794,311 B2 | 9/2004 | Huang et al. |
| 6,796,314 B1 | 9/2004 | Graff et al. |
| 6,797,189 B2 | 9/2004 | Hung et al. |
| 6,800,336 B1 | 10/2004 | Fornsel et al. |
| 6,800,830 B2 | 10/2004 | Mahawili |
| 6,802,944 B2 | 10/2004 | Ahmad et al. |
| 6,808,564 B2 | 10/2004 | Dietze |
| 6,808,747 B1 | 10/2004 | Shih et al. |
| 6,808,748 B2 | 10/2004 | Kapoor et al. |
| 6,815,633 B1 | 11/2004 | Chen et al. |
| 6,821,571 B2 | 11/2004 | Huang |
| 6,823,589 B2 | 11/2004 | White et al. |
| 6,828,241 B2 | 12/2004 | Kholodenko et al. |
| 6,830,624 B2 | 12/2004 | Janakiraman et al. |
| 6,835,995 B2 | 12/2004 | Li |
| 6,846,745 B1 | 1/2005 | Papasouliotis et al. |
| 6,849,854 B2 | 2/2005 | Sainty |
| 6,852,550 B2 | 2/2005 | Tuttle et al. |
| 6,852,584 B1 | 2/2005 | Chen et al. |
| 6,853,533 B2 | 2/2005 | Parkhe et al. |
| 6,858,153 B2 | 2/2005 | Bjorkman et al. |
| 6,861,097 B1 | 3/2005 | Goosey et al. |
| 6,861,332 B2 | 3/2005 | Park et al. |
| 6,869,880 B2 | 3/2005 | Krishnaraj et al. |
| 6,875,280 B2 | 4/2005 | Ikeda et al. |
| 6,878,206 B2 | 4/2005 | Tzu et al. |
| 6,879,981 B2 | 4/2005 | Rothschild et al. |
| 6,886,491 B2 | 5/2005 | Kim et al. |
| 6,892,669 B2 | 5/2005 | Xu et al. |
| 6,893,967 B1 | 5/2005 | Wright et al. |
| 6,897,532 B1 | 5/2005 | Schwarz et al. |
| 6,900,596 B2 | 5/2005 | Yang et al. |
| 6,903,511 B2 | 6/2005 | Chistyakov |
| 6,908,862 B2 | 6/2005 | Li et al. |
| 6,911,112 B2 | 6/2005 | An |
| 6,911,401 B2 | 6/2005 | Khandan et al. |
| 6,916,399 B1 | 7/2005 | Rozenzon et al. |
| 6,921,556 B2 | 7/2005 | Shimizu et al. |
| 6,924,191 B2 | 8/2005 | Liu et al. |
| 6,930,047 B2 | 8/2005 | Yamazaki |
| 6,935,269 B2 | 8/2005 | Lee et al. |
| 6,942,753 B2 | 9/2005 | Choi et al. |
| 6,946,033 B2 | 9/2005 | Tsuei et al. |
| 6,951,821 B2 | 10/2005 | Hamelin et al. |
| 6,958,175 B2 | 10/2005 | Sakamoto et al. |
| 6,958,286 B2 | 10/2005 | Chen et al. |
| 6,995,073 B2 | 2/2006 | Liou |
| 7,017,269 B2 | 3/2006 | White et al. |
| 7,018,941 B2 | 3/2006 | Cui et al. |
| 7,030,034 B2 | 4/2006 | Fucsko et al. |
| 7,049,200 B2 | 5/2006 | Arghavani et al. |
| 7,052,553 B1 | 5/2006 | Shih et al. |
| 7,071,532 B2 | 7/2006 | Geffken et al. |
| 7,084,070 B1 | 8/2006 | Lee et al. |
| 7,115,525 B2 | 10/2006 | Abatchev et al. |
| 7,122,949 B2 | 10/2006 | Strikovski |
| 7,138,767 B2 | 11/2006 | Chen et al. |
| 7,145,725 B2 | 12/2006 | Hasel et al. |
| 7,148,155 B1 | 12/2006 | Tarafdar et al. |
| 7,166,233 B2 | 1/2007 | Johnson et al. |
| 7,183,214 B2 | 2/2007 | Nam et al. |
| 7,196,342 B2 | 3/2007 | Ershov et al. |
| 7,226,805 B2 | 6/2007 | Hallin et al. |
| 7,235,137 B2 | 6/2007 | Kitayama et al. |
| 7,244,474 B2 | 7/2007 | Hanawa et al. |
| 7,252,011 B2 | 8/2007 | Traverso |
| 7,252,716 B2 | 8/2007 | Kim et al. |
| 7,253,123 B2 | 8/2007 | Arghavani et al. |
| 7,256,370 B2 | 8/2007 | Guiver |
| 7,274,004 B2 | 9/2007 | Benjamin et al. |
| 7,288,482 B2 | 10/2007 | Panda et al. |
| 7,291,360 B2 | 11/2007 | Hanawa et al. |
| 7,316,761 B2 | 1/2008 | Doan et al. |

(56) References Cited

U.S. PATENT DOCUMENTS

| | | |
|---|---|---|
| 7,329,608 B2 | 2/2008 | Babayan et al. |
| 7,341,633 B2 | 3/2008 | Lubomirsky et al. |
| 7,344,912 B1 | 3/2008 | Okoroanyanwu |
| 7,358,192 B2 | 4/2008 | Merry et al. |
| 7,361,865 B2 | 4/2008 | Maki et al. |
| 7,364,956 B2 | 4/2008 | Saito |
| 7,365,016 B2 | 4/2008 | Ouellet et al. |
| 7,396,480 B2 | 7/2008 | Kao et al. |
| 7,396,773 B1 | 7/2008 | Blosse et al. |
| 7,416,989 B1 | 8/2008 | Liu et al. |
| 7,465,358 B2 | 12/2008 | Weidman et al. |
| 7,465,953 B1 | 12/2008 | Koh et al. |
| 7,468,319 B2 | 12/2008 | Lee |
| 7,479,303 B2 | 1/2009 | Byun et al. |
| 7,484,473 B2 | 2/2009 | Keller et al. |
| 7,488,688 B2 | 2/2009 | Chung et al. |
| 7,494,545 B2 | 2/2009 | Lam et al. |
| 7,500,445 B2 | 3/2009 | Zhao et al. |
| 7,513,214 B2 | 4/2009 | Okumura et al. |
| 7,520,957 B2 | 4/2009 | Kao et al. |
| 7,553,756 B2 | 6/2009 | Hayashi et al. |
| 7,575,007 B2 | 8/2009 | Tang et al. |
| 7,581,511 B2 | 9/2009 | Mardian et al. |
| 7,604,708 B2 | 10/2009 | Wood et al. |
| 7,611,980 B2 | 11/2009 | Wells |
| 7,628,897 B2 | 12/2009 | Mungekar et al. |
| 7,658,799 B2 | 2/2010 | Ishikawa et al. |
| 7,682,518 B2 | 3/2010 | Chandrachood et al. |
| 7,695,590 B2 | 4/2010 | Hanawa et al. |
| 7,708,859 B2 | 5/2010 | Huang et al. |
| 7,722,925 B2 | 5/2010 | White et al. |
| 7,723,221 B2 | 5/2010 | Hayashi |
| 7,749,326 B2 | 7/2010 | Kim et al. |
| 7,780,790 B2 | 8/2010 | Nogami |
| 7,785,672 B2 | 8/2010 | Choi et al. |
| 7,790,634 B2 | 9/2010 | Munro et al. |
| 7,806,077 B2 | 10/2010 | Lee et al. |
| 7,806,078 B2 | 10/2010 | Yoshida |
| 7,807,578 B2 | 10/2010 | Bencher et al. |
| 7,825,038 B2 | 11/2010 | Ingle et al. |
| 7,837,828 B2 | 11/2010 | Ikeda et al. |
| 7,845,309 B2 | 12/2010 | Condrashoff et al. |
| 7,867,926 B2 | 1/2011 | Satoh et al. |
| 7,915,139 B1 | 3/2011 | Lang et al. |
| 7,922,863 B2 | 4/2011 | Ripley |
| 7,932,181 B2 | 4/2011 | Singh et al. |
| 7,939,422 B2 | 5/2011 | Ingle et al. |
| 7,968,441 B2 | 6/2011 | Xu |
| 7,976,631 B2 | 7/2011 | Burrows |
| 7,977,249 B1 | 7/2011 | Liu |
| 7,981,806 B2 | 7/2011 | Jung |
| 7,989,365 B2 | 8/2011 | Park et al. |
| 8,008,166 B2 | 8/2011 | Sanchez et al. |
| 8,048,811 B2 | 11/2011 | Feustel et al. |
| 8,058,179 B1 | 11/2011 | Draeger et al. |
| 8,071,482 B2 | 12/2011 | Kawada |
| 8,074,599 B2 | 12/2011 | Choi et al. |
| 8,076,198 B2 | 12/2011 | Lee et al. |
| 8,083,853 B2 | 12/2011 | Choi et al. |
| 8,114,245 B2 | 2/2012 | Ohmi et al. |
| 8,119,530 B2 | 2/2012 | Hori et al. |
| 8,133,349 B1 | 3/2012 | Panagopoulos |
| 8,173,228 B2 | 5/2012 | Choi et al. |
| 8,183,134 B2 | 5/2012 | Wu |
| 8,187,486 B1 | 5/2012 | Liu et al. |
| 8,211,808 B2 | 7/2012 | Sapre et al. |
| 8,216,486 B2 | 7/2012 | Dhindsa |
| 8,222,128 B2 | 7/2012 | Sasaki et al. |
| 8,252,194 B2 | 8/2012 | Kiehlbauch et al. |
| 8,272,346 B2 | 9/2012 | Bettencourt et al. |
| 8,295,089 B2 | 10/2012 | Jeong et al. |
| 8,298,627 B2 | 10/2012 | Minami et al. |
| 8,298,959 B2 | 10/2012 | Cheshire |
| 8,309,440 B2 | 11/2012 | Sanchez et al. |
| 8,312,839 B2 | 11/2012 | Baek |
| 8,313,610 B2 | 11/2012 | Dhindsa |
| 8,328,939 B2 | 12/2012 | Choi et al. |
| 8,329,262 B2 | 12/2012 | Miller et al. |
| 8,336,188 B2 | 12/2012 | Monteen |
| 8,357,435 B2 | 1/2013 | Lubomirsky |
| 8,368,308 B2 | 2/2013 | Banna et al. |
| 8,390,980 B2 | 3/2013 | Sansoni et al. |
| 8,427,067 B2 | 4/2013 | Espiau et al. |
| 8,435,902 B2 | 5/2013 | Tang et al. |
| 8,440,523 B1 | 5/2013 | Guillorn et al. |
| 8,466,073 B2 | 6/2013 | Wang et al. |
| 8,475,674 B2 | 7/2013 | Thadani et al. |
| 8,480,850 B2 | 7/2013 | Tyler et al. |
| 8,491,805 B2 | 7/2013 | Kushibiki et al. |
| 8,501,629 B2 | 8/2013 | Tang et al. |
| 8,506,713 B2 | 8/2013 | Takagi |
| 8,512,509 B2 | 8/2013 | Bera et al. |
| 8,528,889 B2 | 9/2013 | Sansoni et al. |
| 8,540,844 B2 | 9/2013 | Hudson et al. |
| 8,551,891 B2 | 10/2013 | Liang |
| 8,573,152 B2 | 11/2013 | De La Llera |
| 8,622,021 B2 | 1/2014 | Taylor et al. |
| 8,623,471 B2 | 1/2014 | Tyler et al. |
| 8,633,423 B2 | 1/2014 | Lin et al. |
| 8,642,481 B2 | 2/2014 | Wang et al. |
| 8,652,298 B2 | 2/2014 | Dhindsa et al. |
| 8,668,836 B2 | 3/2014 | Mizukami et al. |
| 8,679,982 B2 | 3/2014 | Wang et al. |
| 8,679,983 B2 | 3/2014 | Wang et al. |
| 8,691,023 B2 | 4/2014 | Bao et al. |
| 8,702,902 B2 | 4/2014 | Blom et al. |
| 8,741,778 B2 | 6/2014 | Yang et al. |
| 8,747,680 B1 | 6/2014 | Deshpande |
| 8,748,322 B1 | 6/2014 | Fung et al. |
| 8,765,574 B2 | 7/2014 | Zhang et al. |
| 8,771,536 B2 | 7/2014 | Zhang et al. |
| 8,771,539 B2 | 7/2014 | Zhang et al. |
| 8,772,888 B2 | 7/2014 | Jung et al. |
| 8,778,079 B2 | 7/2014 | Begarney et al. |
| 8,801,952 B1 | 8/2014 | Wang et al. |
| 8,802,572 B2 | 8/2014 | Nemani et al. |
| 8,808,563 B2 | 8/2014 | Wang et al. |
| 8,815,720 B2 | 8/2014 | Godet et al. |
| 8,846,163 B2 | 9/2014 | Kao et al. |
| 8,869,742 B2 | 10/2014 | Dhindsa |
| 8,871,651 B1 | 10/2014 | Choi et al. |
| 8,888,087 B2 | 11/2014 | Okabe et al. |
| 8,894,767 B2 | 11/2014 | Goradia et al. |
| 8,895,449 B1 | 11/2014 | Zhu et al. |
| 8,900,364 B2 | 12/2014 | Wright |
| 8,921,234 B2 * | 12/2014 | Liu .................. H01L 21/32136 156/345.13 |
| 8,927,390 B2 | 1/2015 | Sapre et al. |
| 8,937,017 B2 | 1/2015 | Cheshire et al. |
| 8,945,414 B1 | 2/2015 | Su et al. |
| 8,951,429 B1 | 2/2015 | Liu et al. |
| 8,956,980 B1 | 2/2015 | Chen et al. |
| 8,969,212 B2 | 3/2015 | Ren et al. |
| 8,970,114 B2 | 3/2015 | Busche et al. |
| 8,980,005 B2 | 3/2015 | Carlson et al. |
| 8,980,758 B1 | 3/2015 | Ling et al. |
| 8,980,763 B2 | 3/2015 | Wang et al. |
| 8,992,723 B2 | 3/2015 | Sorensen et al. |
| 8,999,656 B2 | 4/2015 | Jirstrom et al. |
| 8,999,839 B2 | 4/2015 | Su et al. |
| 8,999,856 B2 | 4/2015 | Zhang et al. |
| 9,012,302 B2 | 4/2015 | Sapre et al. |
| 9,017,481 B1 | 4/2015 | Pettinger et al. |
| 9,023,732 B2 | 5/2015 | Wang et al. |
| 9,023,734 B2 | 5/2015 | Chen et al. |
| 9,034,770 B2 | 5/2015 | Park et al. |
| 9,040,422 B2 | 5/2015 | Wang et al. |
| 9,064,815 B2 | 6/2015 | Zhang et al. |
| 9,064,816 B2 | 6/2015 | Kim et al. |
| 9,072,158 B2 | 6/2015 | Ikeda et al. |
| 9,093,371 B2 | 7/2015 | Wang et al. |
| 9,093,389 B2 | 7/2015 | Nemani |
| 9,093,390 B2 | 7/2015 | Wang et al. |
| 9,111,877 B2 | 8/2015 | Chen et al. |

(56) References Cited

U.S. PATENT DOCUMENTS

| | | |
|---|---|---|
| 9,111,907 B2 | 8/2015 | Kamineni |
| 9,114,438 B2 | 8/2015 | Hoinkis et al. |
| 9,117,855 B2 | 8/2015 | Cho et al. |
| 9,132,436 B2 | 9/2015 | Liang et al. |
| 9,136,273 B1 | 9/2015 | Purayath et al. |
| 9,144,147 B2 | 9/2015 | Yang et al. |
| 9,153,442 B2 | 10/2015 | Wang et al. |
| 9,159,606 B1 | 10/2015 | Purayath et al. |
| 9,165,783 B2 | 10/2015 | Nemani et al. |
| 9,165,786 B1 | 10/2015 | Purayath et al. |
| 9,184,055 B2 | 11/2015 | Wang et al. |
| 9,190,290 B2 | 11/2015 | Xue et al. |
| 9,190,293 B2 | 11/2015 | Wang et al. |
| 9,190,302 B2 | 11/2015 | Ni |
| 9,202,708 B1 | 12/2015 | Chen et al. |
| 9,209,012 B2 | 12/2015 | Chen et al. |
| 9,236,265 B2 | 1/2016 | Korolik et al. |
| 9,236,266 B2 | 1/2016 | Zhang et al. |
| 9,240,315 B1 | 1/2016 | Hsieh et al. |
| 9,245,762 B2 | 1/2016 | Zhang et al. |
| 9,263,278 B2 | 2/2016 | Purayath et al. |
| 9,269,590 B2 | 2/2016 | Luere et al. |
| 9,275,834 B1 | 3/2016 | Park et al. |
| 9,287,095 B2 | 3/2016 | Nguyen et al. |
| 9,287,134 B2 | 3/2016 | Wang et al. |
| 9,293,568 B2 | 3/2016 | Ko |
| 9,299,537 B2 | 3/2016 | Kobayashi et al. |
| 9,299,538 B2 | 3/2016 | Kobayashi et al. |
| 9,299,575 B2 | 3/2016 | Park et al. |
| 9,299,582 B2 | 3/2016 | Ingle et al. |
| 9,299,583 B1 | 3/2016 | Wang et al. |
| 9,309,598 B2 | 4/2016 | Wang et al. |
| 9,324,576 B2 | 4/2016 | Zhang et al. |
| 9,343,272 B1 | 5/2016 | Pandit et al. |
| 9,343,327 B2 | 5/2016 | Zhange et al. |
| 9,349,605 B1 | 5/2016 | Xu et al. |
| 9,355,856 B2 | 5/2016 | Wang et al. |
| 9,355,862 B2 | 5/2016 | Pandit et al. |
| 9,355,863 B2 | 5/2016 | Chen et al. |
| 9,355,922 B2 | 5/2016 | Park et al. |
| 9,362,130 B2 | 6/2016 | Ingle et al. |
| 9,362,163 B2 | 6/2016 | Danek et al. |
| 9,368,364 B2 | 6/2016 | Park et al. |
| 9,373,517 B2 | 6/2016 | Yang et al. |
| 9,373,522 B1 | 6/2016 | Wang et al. |
| 9,378,969 B2 | 6/2016 | Hsu et al. |
| 9,378,978 B2 | 6/2016 | Purayath et al. |
| 9,384,997 B2 | 7/2016 | Ren et al. |
| 9,385,028 B2 | 7/2016 | Nemani et al. |
| 9,390,937 B2 | 7/2016 | Chen et al. |
| 9,396,961 B2 | 7/2016 | Arghavani et al. |
| 9,396,989 B2 | 7/2016 | Purayath et al. |
| 9,406,523 B2 | 8/2016 | Chen et al. |
| 9,412,608 B2 | 8/2016 | Wang et al. |
| 9,418,858 B2 | 8/2016 | Wang et al. |
| 9,425,041 B2 | 8/2016 | Berry et al. |
| 9,425,058 B2 | 8/2016 | Kim et al. |
| 9,431,268 B2 | 8/2016 | Lill et al. |
| 9,343,358 B1 | 9/2016 | Montgomery |
| 9,437,451 B2 | 9/2016 | Chen et al. |
| 9,443,749 B2 | 9/2016 | Smith |
| 9,449,845 B2 | 9/2016 | Liu et al. |
| 9,449,846 B2 | 9/2016 | Liu et al. |
| 9,449,850 B2 | 9/2016 | Wang et al. |
| 9,460,959 B1 | 10/2016 | Xie et al. |
| 9,466,469 B2 | 10/2016 | Khaja |
| 9,472,412 B2 | 10/2016 | Zhang et al. |
| 9,472,417 B2 | 10/2016 | Ingle et al. |
| 9,478,432 B2 | 10/2016 | Chen et al. |
| 9,478,433 B1 | 10/2016 | Zhou et al. |
| 9,478,434 B2 | 10/2016 | Wang et al. |
| 9,493,879 B2 | 11/2016 | Hoinkis et al. |
| 9,496,167 B2 | 11/2016 | Purayath et al. |
| 9,499,898 B2 | 11/2016 | Nguyen et al. |
| 9,502,258 B2 | 11/2016 | Xue et al. |
| 9,508,529 B2 | 11/2016 | Valcore et al. |
| 9,520,303 B2 | 12/2016 | Wang et al. |
| 9,543,163 B2 | 1/2017 | Ling et al. |
| 9,564,296 B2 | 2/2017 | Kobayashi et al. |
| 9,564,338 B1 | 2/2017 | Zhang et al. |
| 9,576,788 B2 | 2/2017 | Liu et al. |
| 9,576,809 B2 | 2/2017 | Korolik et al. |
| 9,601,319 B1 | 3/2017 | Bravo et al. |
| 9,607,856 B2 | 3/2017 | Wang et al. |
| 9,613,822 B2 | 4/2017 | Chen et al. |
| 9,659,753 B2 | 5/2017 | Cho et al. |
| 9,659,791 B2 | 5/2017 | Wang et al. |
| 9,659,792 B2 | 5/2017 | Wang et al. |
| 9,666,449 B2 | 5/2017 | Koval et al. |
| 9,691,645 B2 | 6/2017 | Ayers |
| 9,704,723 B2 | 7/2017 | Wang et al. |
| 9,711,366 B2 | 7/2017 | Ingle et al. |
| 9,721,789 B1 | 8/2017 | Yang et al. |
| 9,728,437 B2 | 8/2017 | Tran et al. |
| 9,741,593 B2 | 8/2017 | Benjaminson et al. |
| 9,754,800 B2 | 9/2017 | Zhang et al. |
| 9,768,034 B1 | 9/2017 | Xu et al. |
| 9,773,648 B2 | 9/2017 | Cho et al. |
| 9,773,695 B2 | 9/2017 | Purayath et al. |
| 9,779,956 B1 | 10/2017 | Zhang et al. |
| 9,822,009 B2 | 11/2017 | Kagaya et al. |
| 9,831,097 B2 | 11/2017 | Ingle et al. |
| 9,837,249 B2 | 12/2017 | Kobayashi et al. |
| 9,837,284 B2 | 12/2017 | Chen et al. |
| 9,837,286 B2 | 12/2017 | Yang et al. |
| 9,842,744 B2 | 12/2017 | Zhang et al. |
| 9,865,484 B1 | 1/2018 | Citla et al. |
| 9,881,805 B2 | 1/2018 | Li et al. |
| 9,885,117 B2 | 2/2018 | Lubomirsky et al. |
| 9,887,096 B2 | 2/2018 | Park et al. |
| 9,903,020 B2 | 2/2018 | Kim et al. |
| 9,934,942 B1 | 4/2018 | Lubomirsky |
| 9,947,549 B1 | 4/2018 | Park et al. |
| 9,966,240 B2 | 5/2018 | Park et al. |
| 9,978,564 B2 | 5/2018 | Liang et al. |
| 9,991,134 B2 | 6/2018 | Wang et al. |
| 10,026,621 B2 | 7/2018 | Ko et al. |
| 10,032,606 B2 | 7/2018 | Yang et al. |
| 10,043,674 B1 | 8/2018 | Korolik et al. |
| 10,043,684 B1 | 8/2018 | Arnepalli et al. |
| 10,049,891 B1 | 8/2018 | Wang et al. |
| 10,062,578 B2 | 8/2018 | Zhang et al. |
| 10,062,579 B2 | 8/2018 | Chen et al. |
| 10,062,585 B2 | 8/2018 | Lubomirsky |
| 10,062,587 B2 | 8/2018 | Chen et al. |
| 2001/0006093 A1 | 7/2001 | Tabuchi |
| 2001/0008803 A1 | 7/2001 | Takamatsu et al. |
| 2001/0015175 A1 | 8/2001 | Masuda et al. |
| 2001/0015261 A1 | 8/2001 | Kobayashi et al. |
| 2001/0028093 A1 | 10/2001 | Yamazaki et al. |
| 2001/0028922 A1 | 10/2001 | Sandhu |
| 2001/0029891 A1 | 10/2001 | Oh et al. |
| 2001/0030366 A1 | 10/2001 | Nakano et al. |
| 2001/0034106 A1 | 10/2001 | Moise et al. |
| 2001/0034121 A1 | 10/2001 | Fu et al. |
| 2001/0035124 A1 | 11/2001 | Okayama et al. |
| 2001/0036706 A1 | 11/2001 | Kitamura |
| 2001/0037856 A1 | 11/2001 | Park |
| 2001/0037941 A1 | 11/2001 | Thompson |
| 2001/0039921 A1 | 11/2001 | Rolfson et al. |
| 2001/0042512 A1 | 11/2001 | Xu et al. |
| 2001/0047760 A1 | 12/2001 | Moslehi |
| 2001/0053585 A1 | 12/2001 | Kikuchi et al. |
| 2001/0053610 A1 | 12/2001 | Athavale |
| 2001/0054381 A1 | 12/2001 | Umotoy et al. |
| 2001/0054387 A1 | 12/2001 | Frankel et al. |
| 2002/0000202 A1 | 1/2002 | Yuda et al. |
| 2002/0001778 A1 | 1/2002 | Latchford et al. |
| 2002/0009560 A1 | 1/2002 | Ozono |
| 2002/0009885 A1 | 1/2002 | Brankner et al. |
| 2002/0011210 A1 | 1/2002 | Satoh et al. |
| 2002/0011214 A1 | 1/2002 | Kamarehi et al. |
| 2002/0016080 A1 | 2/2002 | Khan et al. |
| 2002/0016085 A1 | 2/2002 | Huang et al. |

(56) References Cited

U.S. PATENT DOCUMENTS

| | | |
|---|---|---|
| 2002/0023899 A1 | 2/2002 | Khater et al. |
| 2002/0028582 A1 | 3/2002 | Nallan et al. |
| 2002/0028585 A1 | 3/2002 | Chung et al. |
| 2002/0029747 A1 | 3/2002 | Powell et al. |
| 2002/0033233 A1 | 3/2002 | Savas |
| 2002/0036143 A1 | 3/2002 | Segawa et al. |
| 2002/0040764 A1 | 4/2002 | Kwan et al. |
| 2002/0040766 A1 | 4/2002 | Takahashi |
| 2002/0043690 A1 | 4/2002 | Doyle et al. |
| 2002/0045966 A1 | 4/2002 | Lee et al. |
| 2002/0046991 A1 | 4/2002 | Smith et al. |
| 2002/0054962 A1 | 5/2002 | Huang |
| 2002/0062954 A1 | 5/2002 | Getchel et al. |
| 2002/0069820 A1 | 6/2002 | Yudovsky |
| 2002/0070414 A1 | 6/2002 | Drescher et al. |
| 2002/0074573 A1 | 6/2002 | Takeuchi et al. |
| 2002/0086501 A1 | 7/2002 | O'Donnell et al. |
| 2002/0090781 A1 | 7/2002 | Skotnicki et al. |
| 2002/0090835 A1 | 7/2002 | Chakravarti et al. |
| 2002/0094378 A1 | 7/2002 | O'Donnell |
| 2002/0094591 A1 | 7/2002 | Sill et al. |
| 2002/0096493 A1 | 7/2002 | Hattori |
| 2002/0098681 A1 | 7/2002 | Hu et al. |
| 2002/0106845 A1 | 8/2002 | Chao et al. |
| 2002/0112819 A1 | 8/2002 | Kamarehi et al. |
| 2002/0124867 A1 | 9/2002 | Kim et al. |
| 2002/0129769 A1 | 9/2002 | Kim et al. |
| 2002/0129902 A1 | 9/2002 | Babayan et al. |
| 2002/0144657 A1 | 10/2002 | Chiang et al. |
| 2002/0153808 A1 | 10/2002 | Skotnicki et al. |
| 2002/0164885 A1 | 11/2002 | Lill et al. |
| 2002/0170678 A1 | 11/2002 | Hayashi et al. |
| 2002/0177322 A1 | 11/2002 | Li et al. |
| 2002/0179248 A1 | 12/2002 | Kabansky et al. |
| 2002/0182878 A1 | 12/2002 | Hirose et al. |
| 2002/0187280 A1 | 12/2002 | Johnson et al. |
| 2002/0187655 A1 | 12/2002 | Tan et al. |
| 2003/0000647 A1 | 1/2003 | Yudovsky et al. |
| 2003/0003757 A1 | 1/2003 | Naltan et al. |
| 2003/0007910 A1 | 1/2003 | Lazarovich et al. |
| 2003/0010645 A1 | 1/2003 | Ting et al. |
| 2003/0019428 A1 | 1/2003 | Ku et al. |
| 2003/0019580 A1 | 1/2003 | Strang |
| 2003/0026060 A1 | 2/2003 | Hiramatsu et al. |
| 2003/0029566 A1 | 2/2003 | Roth |
| 2003/0029567 A1 | 2/2003 | Dhindsa et al. |
| 2003/0029715 A1 | 2/2003 | Yu et al. |
| 2003/0031905 A1 | 2/2003 | Saito et al. |
| 2003/0032284 A1 | 2/2003 | Enomoto et al. |
| 2003/0038127 A1 | 2/2003 | Liu et al. |
| 2003/0038305 A1 | 2/2003 | Wasshuber |
| 2003/0054608 A1 | 3/2003 | Tseng et al. |
| 2003/0066482 A1 | 4/2003 | Pokharna et al. |
| 2003/0071035 A1 | 4/2003 | Brailove |
| 2003/0072639 A1 | 4/2003 | White et al. |
| 2003/0075808 A1 | 4/2003 | Inoue et al. |
| 2003/0077857 A1 | 4/2003 | Xia et al. |
| 2003/0077909 A1 | 4/2003 | Jiwari |
| 2003/0079686 A1 | 5/2003 | Chen et al. |
| 2003/0087488 A1 | 5/2003 | Fink |
| 2003/0087531 A1 | 5/2003 | Kang et al. |
| 2003/0091938 A1 | 5/2003 | Fairbairn et al. |
| 2003/0094134 A1 | 5/2003 | Minami et al. |
| 2003/0098125 A1 | 5/2003 | An |
| 2003/0109143 A1 | 6/2003 | Hsieh et al. |
| 2003/0116087 A1 | 6/2003 | Nguyen et al. |
| 2003/0116439 A1 | 6/2003 | Seo et al. |
| 2003/0121608 A1 | 7/2003 | Chen et al. |
| 2003/0121609 A1 | 7/2003 | Ohmi et al. |
| 2003/0124465 A1 | 7/2003 | Lee et al. |
| 2003/0124842 A1 | 7/2003 | Hytros et al. |
| 2003/0127049 A1 | 7/2003 | Han et al. |
| 2003/0127740 A1 | 7/2003 | Hsu et al. |
| 2003/0129106 A1 | 7/2003 | Sorensen et al. |
| 2003/0129827 A1 | 7/2003 | Lee et al. |
| 2003/0132319 A1 | 7/2003 | Hytros et al. |
| 2003/0140844 A1 | 7/2003 | Maa et al. |
| 2003/0143328 A1 | 7/2003 | Chen et al. |
| 2003/0148035 A1 | 8/2003 | Lingampalli |
| 2003/0150530 A1 | 8/2003 | Lin et al. |
| 2003/0152691 A1 | 8/2003 | Baude |
| 2003/0159307 A1 | 8/2003 | Sago et al. |
| 2003/0164226 A1 | 9/2003 | Kanno et al. |
| 2003/0168439 A1 | 9/2003 | Kanno et al. |
| 2003/0170945 A1 | 9/2003 | Igeta et al. |
| 2003/0173333 A1 | 9/2003 | Wang et al. |
| 2003/0173347 A1 | 9/2003 | Guiver |
| 2003/0173675 A1 | 9/2003 | Watanabe |
| 2003/0181040 A1 | 9/2003 | Ivanov et al. |
| 2003/0183244 A1 | 10/2003 | Rossman |
| 2003/0190426 A1 | 10/2003 | Padhi et al. |
| 2003/0196760 A1 | 10/2003 | Tyler et al. |
| 2003/0199170 A1 | 10/2003 | Li |
| 2003/0200929 A1 | 10/2003 | Otsuki |
| 2003/0205329 A1 | 11/2003 | Gujer et al. |
| 2003/0205479 A1 | 11/2003 | Lin et al. |
| 2003/0209323 A1 | 11/2003 | Yokogaki et al. |
| 2003/0215570 A1 | 11/2003 | Seutter et al. |
| 2003/0215963 A1 | 11/2003 | AmRhein et al. |
| 2003/0216044 A1 | 11/2003 | Lin et al. |
| 2003/0221780 A1 | 12/2003 | Lei et al. |
| 2003/0224217 A1 | 12/2003 | Byun et al. |
| 2003/0224617 A1 | 12/2003 | Baek et al. |
| 2003/0230385 A1 | 12/2003 | Bach et al. |
| 2004/0003828 A1 | 1/2004 | Jackson |
| 2004/0005726 A1 | 1/2004 | Huang |
| 2004/0018304 A1 | 1/2004 | Chung et al. |
| 2004/0020801 A1 | 2/2004 | Solling |
| 2004/0026371 A1 | 2/2004 | Nguyen et al. |
| 2004/0033678 A1 | 2/2004 | Arghavani et al. |
| 2004/0033684 A1 | 2/2004 | Li |
| 2004/0050328 A1 | 3/2004 | Kumagai et al. |
| 2004/0058070 A1 | 3/2004 | Takeuchi et al. |
| 2004/0058293 A1 | 3/2004 | Nguyen et al. |
| 2004/0060514 A1 | 4/2004 | Janakiraman et al. |
| 2004/0061447 A1 | 4/2004 | Saigusa et al. |
| 2004/0069225 A1 | 4/2004 | Fairbairn et al. |
| 2004/0070346 A1 | 4/2004 | Choi |
| 2004/0072446 A1 | 4/2004 | Liu et al. |
| 2004/0076529 A1 | 4/2004 | Gnauck et al. |
| 2004/0083967 A1 | 5/2004 | Yuda et al. |
| 2004/0087139 A1 | 5/2004 | Yeh et al. |
| 2004/0092063 A1 | 5/2004 | Okumura |
| 2004/0099285 A1 | 5/2004 | Wange et al. |
| 2004/0099378 A1 | 5/2004 | Kim et al. |
| 2004/0101667 A1 | 5/2004 | O'Loughlin et al. |
| 2004/0107908 A1 | 6/2004 | Collins et al. |
| 2004/0108067 A1 | 6/2004 | Fischione et al. |
| 2004/0108068 A1 | 6/2004 | Senzaki et al. |
| 2004/0115876 A1 | 6/2004 | Goundar et al. |
| 2004/0124280 A1 | 7/2004 | Shih et al. |
| 2004/0129671 A1 | 7/2004 | Ji et al. |
| 2004/0137161 A1 | 7/2004 | Segawa et al. |
| 2004/0140053 A1 | 7/2004 | Srivastava et al. |
| 2004/0144311 A1 | 7/2004 | Chen et al. |
| 2004/0144490 A1 | 7/2004 | Zhao et al. |
| 2004/0147126 A1 | 7/2004 | Yamashita et al. |
| 2004/0149223 A1 | 8/2004 | Collison et al. |
| 2004/0149394 A1 | 8/2004 | Doan et al. |
| 2004/0152342 A1 | 8/2004 | Li |
| 2004/0154535 A1 | 8/2004 | Chen et al. |
| 2004/0157444 A1 | 8/2004 | Chiu |
| 2004/0161921 A1 | 8/2004 | Ryu |
| 2004/0175913 A1 | 9/2004 | Johnson et al. |
| 2004/0175929 A1 | 9/2004 | Schmitt et al. |
| 2004/0182315 A1 | 9/2004 | Laflamme et al. |
| 2004/0187787 A1 | 9/2004 | Dawson |
| 2004/0192032 A1 | 9/2004 | Ohmori et al. |
| 2004/0194799 A1 | 10/2004 | Kim et al. |
| 2004/0195216 A1 | 10/2004 | Strang |
| 2004/0200499 A1 | 10/2004 | Harvey |
| 2004/0211357 A1 | 10/2004 | Gadgil et al. |
| 2004/0219723 A1 | 11/2004 | Peng et al. |
| 2004/0219737 A1 | 11/2004 | Quon |

(56) References Cited

U.S. PATENT DOCUMENTS

| | | |
|---|---|---|
| 2004/0219789 A1 | 11/2004 | Wood et al. |
| 2004/0221809 A1 | 11/2004 | Ohmi et al. |
| 2004/0231706 A1 | 11/2004 | Bhatnagar et al. |
| 2004/0237897 A1 | 12/2004 | Hanawa et al. |
| 2004/0263827 A1 | 12/2004 | Xu |
| 2005/0000432 A1 | 1/2005 | Keller et al. |
| 2005/0001276 A1 | 1/2005 | Gao et al. |
| 2005/0003676 A1 | 1/2005 | Ho et al. |
| 2005/0009340 A1 | 1/2005 | Saijo et al. |
| 2005/0009358 A1 | 1/2005 | Choi et al. |
| 2005/0026430 A1 | 2/2005 | Kim et al. |
| 2005/0026431 A1 | 2/2005 | Kazumi et al. |
| 2005/0035455 A1 | 2/2005 | Hu et al. |
| 2005/0039679 A1 | 2/2005 | Kleshock |
| 2005/0051094 A1 | 3/2005 | Schaepkens et al. |
| 2005/0056218 A1 | 3/2005 | Sun et al. |
| 2005/0073051 A1 | 4/2005 | Yamamoto et al. |
| 2005/0079706 A1 | 4/2005 | Kumar et al. |
| 2005/0087517 A1 | 4/2005 | Ott et al. |
| 2005/0090078 A1 | 4/2005 | Ishihara |
| 2005/0090120 A1 | 4/2005 | Hasegawa et al. |
| 2005/0098111 A1 | 5/2005 | Shimizu et al. |
| 2005/0103267 A1 | 5/2005 | Hur et al. |
| 2005/0105991 A1 | 5/2005 | Hofmeister et al. |
| 2005/0109279 A1 | 5/2005 | Suzuki |
| 2005/0112876 A1 | 5/2005 | Wu |
| 2005/0112901 A1 | 5/2005 | Ji et al. |
| 2005/0123690 A1 | 6/2005 | Derderian et al. |
| 2005/0136188 A1 | 6/2005 | Chang |
| 2005/0145341 A1 | 7/2005 | Suzuki |
| 2005/0164479 A1 | 7/2005 | Perng et al. |
| 2005/0167394 A1 | 8/2005 | Liu et al. |
| 2005/0176258 A1 | 8/2005 | Hirose et al. |
| 2005/0178746 A1 | 8/2005 | Gorin |
| 2005/0181588 A1 | 8/2005 | Kim |
| 2005/0183666 A1 | 8/2005 | Tsuji et al. |
| 2005/0194094 A1 | 9/2005 | Yasaka |
| 2005/0196967 A1 | 9/2005 | Savas et al. |
| 2005/0199489 A1 | 9/2005 | Stevens et al. |
| 2005/0205110 A1 | 9/2005 | Kao et al. |
| 2005/0205862 A1 | 9/2005 | Koemtzopoulos et al. |
| 2005/0208215 A1 | 9/2005 | Eguchi et al. |
| 2005/0208217 A1 | 9/2005 | Shinriki et al. |
| 2005/0214477 A1 | 9/2005 | Hanawa et al. |
| 2005/0217582 A1 | 10/2005 | Kim et al. |
| 2005/0218507 A1 | 10/2005 | Kao et al. |
| 2005/0219786 A1 | 10/2005 | Brown et al. |
| 2005/0221552 A1 | 10/2005 | Kao et al. |
| 2005/0224181 A1 | 10/2005 | Merry et al. |
| 2005/0229848 A1 | 10/2005 | Shinriki et al. |
| 2005/0230350 A1 | 10/2005 | Kao et al. |
| 2005/0236694 A1 | 10/2005 | Wu et al. |
| 2005/0238807 A1 | 10/2005 | Lin et al. |
| 2005/0239282 A1 | 10/2005 | Chen et al. |
| 2005/0251990 A1 | 11/2005 | Choi et al. |
| 2005/0266622 A1 | 12/2005 | Arghavani et al. |
| 2005/0266650 A1 | 12/2005 | Ahn et al. |
| 2005/0266691 A1 | 12/2005 | Gu et al. |
| 2005/0269030 A1 | 12/2005 | Kent et al. |
| 2005/0274324 A1 | 12/2005 | Takahashi et al. |
| 2005/0279454 A1 | 12/2005 | Snijders |
| 2005/0283321 A1 | 12/2005 | Yue et al. |
| 2005/0287688 A1 | 12/2005 | Won et al. |
| 2005/0287755 A1 | 12/2005 | Bachmann |
| 2005/0287771 A1 | 12/2005 | Seamons et al. |
| 2006/0000802 A1 | 1/2006 | Kumar et al. |
| 2006/0000805 A1 | 1/2006 | Todorow et al. |
| 2006/0005856 A1 | 1/2006 | Sun et al. |
| 2006/0005930 A1 | 1/2006 | Ikeda et al. |
| 2006/0006057 A1 | 1/2006 | Laermer |
| 2006/0008676 A1 | 1/2006 | Ebata et al. |
| 2006/0011298 A1 | 1/2006 | Lim et al. |
| 2006/0011299 A1 | 1/2006 | Condrashoff et al. |
| 2006/0016783 A1 | 1/2006 | Wu et al. |
| 2006/0019456 A1 | 1/2006 | Bu et al. |
| 2006/0019477 A1 | 1/2006 | Hanawa et al. |
| 2006/0019486 A1 | 1/2006 | Yu et al. |
| 2006/0021574 A1 | 2/2006 | Armour et al. |
| 2006/0021701 A1 | 2/2006 | Tobe et al. |
| 2006/0021703 A1 | 2/2006 | Umotoy et al. |
| 2006/0024954 A1 | 2/2006 | Wu et al. |
| 2006/0024956 A1 | 2/2006 | Zhijian et al. |
| 2006/0033678 A1 | 2/2006 | Lubomirsky et al. |
| 2006/0040055 A1 | 2/2006 | Nguyen et al. |
| 2006/0043066 A1 | 3/2006 | Kamp |
| 2006/0046412 A1 | 3/2006 | Nguyen et al. |
| 2006/0046419 A1 | 3/2006 | Sandhu et al. |
| 2006/0046470 A1 | 3/2006 | Becknell |
| 2006/0051966 A1 | 3/2006 | Or et al. |
| 2006/0051968 A1 | 3/2006 | Joshi et al. |
| 2006/0054184 A1 | 3/2006 | Mozetic et al. |
| 2006/0057828 A1 | 3/2006 | Omura et al. |
| 2006/0060942 A1 | 3/2006 | Minixhofer et al. |
| 2006/0065629 A1 | 3/2006 | Chen et al. |
| 2006/0073349 A1 | 4/2006 | Aihara et al. |
| 2006/0076108 A1 | 4/2006 | Holland et al. |
| 2006/0087644 A1 | 4/2006 | McMillin et al. |
| 2006/0090700 A1 | 5/2006 | Satoh et al. |
| 2006/0093756 A1 | 5/2006 | Rajagopalan et al. |
| 2006/0097397 A1 | 5/2006 | Russell et al. |
| 2006/0102076 A1 | 5/2006 | Smith et al. |
| 2006/0102587 A1 | 5/2006 | Kimura |
| 2006/0118178 A1 | 6/2006 | Desbiolles et al. |
| 2006/0118240 A1 | 6/2006 | Holber et al. |
| 2006/0121724 A1 | 6/2006 | Yue et al. |
| 2006/0124151 A1 | 6/2006 | Yamasaki et al. |
| 2006/0124242 A1 | 6/2006 | Kanarik et al. |
| 2006/0130971 A1 | 6/2006 | Chang et al. |
| 2006/0151115 A1 | 7/2006 | Kim et al. |
| 2006/0157449 A1 | 7/2006 | Takahashi et al. |
| 2006/0162661 A1 | 7/2006 | Jung et al. |
| 2006/0166107 A1 | 7/2006 | Chen et al. |
| 2006/0166515 A1 | 7/2006 | Karim et al. |
| 2006/0169327 A1 | 8/2006 | Shajii et al. |
| 2006/0169410 A1 | 8/2006 | Maeda et al. |
| 2006/0178008 A1 | 8/2006 | Yeh et al. |
| 2006/0183270 A1 | 8/2006 | Humpston |
| 2006/0185592 A1 | 8/2006 | Matsuura |
| 2006/0191479 A1 | 8/2006 | Mizukami et al. |
| 2006/0191637 A1 | 8/2006 | Zajac et al. |
| 2006/0207504 A1 | 9/2006 | Hasebe et al. |
| 2006/0207595 A1 | 9/2006 | Ohmi et al. |
| 2006/0207971 A1 | 9/2006 | Moriya et al. |
| 2006/0210723 A1 | 9/2006 | Ishizaka |
| 2006/0215347 A1 | 9/2006 | Wakabayashi et al. |
| 2006/0216878 A1 | 9/2006 | Lee |
| 2006/0219360 A1 | 10/2006 | Iwasaki |
| 2006/0222481 A1 | 10/2006 | Foree |
| 2006/0226121 A1 | 10/2006 | Aoi |
| 2006/0228889 A1 | 10/2006 | Edelberg et al. |
| 2006/0240661 A1 | 10/2006 | Annapragada et al. |
| 2006/0244107 A1 | 11/2006 | Sugihara |
| 2006/0245852 A1 | 11/2006 | Iwabuchi |
| 2006/0246217 A1 | 11/2006 | Weidman et al. |
| 2006/0251800 A1 | 11/2006 | Weidman et al. |
| 2006/0251801 A1 | 11/2006 | Weidman et al. |
| 2006/0252252 A1 | 11/2006 | Zhu et al. |
| 2006/0252265 A1 | 11/2006 | Jin et al. |
| 2006/0254716 A1 | 11/2006 | Mosden et al. |
| 2006/0260750 A1 | 11/2006 | Rueger |
| 2006/0261490 A1 | 11/2006 | Su et al. |
| 2006/0264043 A1 | 11/2006 | Stewart et al. |
| 2006/0266288 A1 | 11/2006 | Choi |
| 2006/0286774 A1 | 12/2006 | Singh et al. |
| 2006/0292846 A1 | 12/2006 | Pinto et al. |
| 2007/0022952 A1 | 2/2007 | Ritchie et al. |
| 2007/0025907 A1 | 2/2007 | Rezeq |
| 2007/0039548 A1 | 2/2007 | Johnson |
| 2007/0048977 A1 | 3/2007 | Lee et al. |
| 2007/0051471 A1 | 3/2007 | Kawaguchi et al. |
| 2007/0056925 A1 | 3/2007 | Liu et al. |
| 2007/0062453 A1 | 3/2007 | Ishikawa |
| 2007/0066084 A1 | 3/2007 | Wajda et al. |
| 2007/0071888 A1 | 3/2007 | Shanmugasundram et al. |

(56) References Cited

U.S. PATENT DOCUMENTS

| | | |
|---|---|---|
| 2007/0072408 A1 | 3/2007 | Enomoto et al. |
| 2007/0077737 A1 | 4/2007 | Kobayashi |
| 2007/0079758 A1 | 4/2007 | Holland et al. |
| 2007/0090325 A1 | 4/2007 | Hwang et al. |
| 2007/0099428 A1 | 5/2007 | Shamiryan et al. |
| 2007/0099431 A1 | 5/2007 | Li |
| 2007/0099438 A1 | 5/2007 | Ye et al. |
| 2007/0107750 A1 | 5/2007 | Sawin et al. |
| 2007/0108404 A1 | 5/2007 | Stewart et al. |
| 2007/0111519 A1 | 5/2007 | Lubomirsky et al. |
| 2007/0117396 A1 | 5/2007 | Wu et al. |
| 2007/0119370 A1 | 5/2007 | Ma et al. |
| 2007/0119371 A1 | 5/2007 | Ma et al. |
| 2007/0123051 A1 | 5/2007 | Arghavani et al. |
| 2007/0128864 A1 | 6/2007 | Ma |
| 2007/0131274 A1 | 6/2007 | Stollwerck et al. |
| 2007/0145023 A1 | 6/2007 | Holber et al. |
| 2007/0154838 A1 | 7/2007 | Lee |
| 2007/0163440 A1 | 7/2007 | Kim et al. |
| 2007/0175861 A1 | 8/2007 | Hwang et al. |
| 2007/0181057 A1 | 8/2007 | Lam et al. |
| 2007/0193515 A1 | 8/2007 | Jeon et al. |
| 2007/0197028 A1 | 8/2007 | Byun et al. |
| 2007/0207275 A1 | 9/2007 | Nowak et al. |
| 2007/0212288 A1 | 9/2007 | Holst |
| 2007/0221620 A1 | 9/2007 | Sakthivel et al. |
| 2007/0227554 A1 | 10/2007 | Satoh et al. |
| 2007/0231109 A1 | 10/2007 | Pak et al. |
| 2007/0232071 A1 | 10/2007 | Balseanu et al. |
| 2007/0235134 A1 | 10/2007 | Limuro |
| 2007/0238199 A1 | 10/2007 | Yamashita |
| 2007/0238321 A1 | 10/2007 | Futase et al. |
| 2007/0243685 A1 | 10/2007 | Jiang et al. |
| 2007/0243714 A1 | 10/2007 | Shin et al. |
| 2007/0254169 A1 | 11/2007 | Kamins et al. |
| 2007/0259467 A1 | 11/2007 | Tweet et al. |
| 2007/0264820 A1 | 11/2007 | Liu |
| 2007/0266946 A1 | 11/2007 | Choi |
| 2007/0277734 A1 | 12/2007 | Lubomirsky et al. |
| 2007/0280816 A1 | 12/2007 | Kurita et al. |
| 2007/0281106 A1 | 12/2007 | Lubomirsky et al. |
| 2007/0287292 A1 | 12/2007 | Li et al. |
| 2007/0296967 A1 | 12/2007 | Gupta et al. |
| 2008/0003836 A1 | 1/2008 | Nishimura et al. |
| 2008/0017104 A1 | 1/2008 | Matyushkin et al. |
| 2008/0020570 A1 | 1/2008 | Naik |
| 2008/0035608 A1 | 2/2008 | Thomas et al. |
| 2008/0044593 A1 | 2/2008 | Seo et al. |
| 2008/0044990 A1 | 2/2008 | Lee |
| 2008/0050538 A1 | 2/2008 | Hirata |
| 2008/0063810 A1 | 3/2008 | Park et al. |
| 2008/0075668 A1 | 3/2008 | Goldstein |
| 2008/0081483 A1 | 4/2008 | Wu |
| 2008/0085604 A1 | 4/2008 | Hoshino et al. |
| 2008/0099147 A1 | 5/2008 | Myo et al. |
| 2008/0099431 A1 | 5/2008 | Kumar et al. |
| 2008/0099876 A1 | 5/2008 | Seto |
| 2008/0100222 A1 | 5/2008 | Lewington et al. |
| 2008/0102570 A1 | 5/2008 | Fischer et al. |
| 2008/0102640 A1 | 5/2008 | Hassan et al. |
| 2008/0104782 A1 | 5/2008 | Hughes |
| 2008/0105555 A1 | 5/2008 | Iwazaki et al. |
| 2008/0115726 A1 | 5/2008 | Ingle et al. |
| 2008/0121970 A1 | 5/2008 | Aritome |
| 2008/0124937 A1 | 5/2008 | Xu et al. |
| 2008/0142831 A1 | 6/2008 | Su |
| 2008/0153306 A1 | 6/2008 | Cho et al. |
| 2008/0156771 A1 | 7/2008 | Jeon et al. |
| 2008/0157225 A1 | 7/2008 | Datta et al. |
| 2008/0160210 A1 | 7/2008 | Yang et al. |
| 2008/0169588 A1 | 7/2008 | Shih et al. |
| 2008/0171407 A1 | 7/2008 | Nakabayashi et al. |
| 2008/0173906 A1 | 7/2008 | Zhu |
| 2008/0176412 A1 | 7/2008 | Komeda |
| 2008/0178797 A1 | 7/2008 | Fodor et al. |
| 2008/0178805 A1 | 7/2008 | Paterson et al. |
| 2008/0182381 A1 | 7/2008 | Kiyotoshi |
| 2008/0182382 A1 | 7/2008 | Ingle et al. |
| 2008/0182383 A1 | 7/2008 | Lee et al. |
| 2008/0196666 A1 | 8/2008 | Toshima |
| 2008/0202688 A1 | 8/2008 | Wu et al. |
| 2008/0202892 A1 | 8/2008 | Smith et al. |
| 2008/0216901 A1 | 9/2008 | Chamberlain et al. |
| 2008/0216958 A1 | 9/2008 | Goto et al. |
| 2008/0230519 A1 | 9/2008 | Takahashi |
| 2008/0233709 A1 | 9/2008 | Conti et al. |
| 2008/0236751 A1 | 10/2008 | Aramaki et al. |
| 2008/0254635 A1 | 10/2008 | Benzel et al. |
| 2008/0261404 A1 | 10/2008 | Kozuka et al. |
| 2008/0264337 A1 | 10/2008 | Sano et al. |
| 2008/0268645 A1 | 10/2008 | Kao et al. |
| 2008/0292798 A1 | 11/2008 | Huh et al. |
| 2008/0293248 A1 | 11/2008 | Park et al. |
| 2009/0000743 A1 | 1/2009 | Ilzuka |
| 2009/0001480 A1 | 1/2009 | Cheng |
| 2009/0004849 A1 | 1/2009 | Eun |
| 2009/0004873 A1 | 1/2009 | Yang |
| 2009/0014127 A1 | 1/2009 | Shah et al. |
| 2009/0014323 A1 | 1/2009 | Yendler et al. |
| 2009/0014324 A1 | 1/2009 | Kawaguchi et al. |
| 2009/0017227 A1 | 1/2009 | Fu et al. |
| 2009/0036292 A1 | 2/2009 | Sun et al. |
| 2009/0045167 A1 | 2/2009 | Maruyama |
| 2009/0072401 A1 | 3/2009 | Arnold et al. |
| 2009/0081878 A1 | 3/2009 | Dhindsa |
| 2009/0084317 A1 | 4/2009 | Wu et al. |
| 2009/0087960 A1 | 4/2009 | Cho et al. |
| 2009/0087979 A1 | 4/2009 | Raghuram |
| 2009/0095222 A1 | 4/2009 | Tam et al. |
| 2009/0095621 A1 | 4/2009 | Kao et al. |
| 2009/0098276 A1 | 4/2009 | Burrows |
| 2009/0098706 A1 | 4/2009 | Kim et al. |
| 2009/0104738 A1 | 4/2009 | Ring et al. |
| 2009/0104782 A1 | 4/2009 | Lu et al. |
| 2009/0111280 A1 | 4/2009 | Kao et al. |
| 2009/0117270 A1 | 5/2009 | Yamasaki et al. |
| 2009/0120464 A1 | 5/2009 | Rasheed et al. |
| 2009/0162647 A1 | 6/2009 | Sun et al. |
| 2009/0170221 A1 | 7/2009 | Jacques et al. |
| 2009/0170331 A1 | 7/2009 | Cheng et al. |
| 2009/0179300 A1 | 7/2009 | Arai |
| 2009/0189246 A1 | 7/2009 | Wu et al. |
| 2009/0189287 A1 | 7/2009 | Yang et al. |
| 2009/0191711 A1 | 7/2009 | Rui et al. |
| 2009/0194233 A1 | 8/2009 | Tamura et al. |
| 2009/0194810 A1 | 8/2009 | Kiyotoshi et al. |
| 2009/0197418 A1 | 8/2009 | Sago et al. |
| 2009/0202721 A1 | 8/2009 | Nogami et al. |
| 2009/0214825 A1 | 8/2009 | Sun et al. |
| 2009/0223928 A1 | 9/2009 | Colpo |
| 2009/0236314 A1 | 9/2009 | Chen |
| 2009/0255902 A1 | 10/2009 | Satoh et al. |
| 2009/0258162 A1 | 10/2009 | Furuta et al. |
| 2009/0269934 A1 | 10/2009 | Kao et al. |
| 2009/0274590 A1 | 11/2009 | Willwerth et al. |
| 2009/0275146 A1 | 11/2009 | Takano et al. |
| 2009/0275205 A1 | 11/2009 | Kiehlbauch et al. |
| 2009/0275206 A1 | 11/2009 | Katz et al. |
| 2009/0277587 A1 | 11/2009 | Lubomirsky et al. |
| 2009/0277874 A1 | 11/2009 | Rui et al. |
| 2009/0280650 A1 | 11/2009 | Lubomirsky et al. |
| 2009/0286400 A1 | 11/2009 | Heo et al. |
| 2009/0286405 A1 | 11/2009 | Okesaku et al. |
| 2009/0293809 A1 | 12/2009 | Cho et al. |
| 2009/0294898 A1 | 12/2009 | Feustel et al. |
| 2009/0317978 A1 | 12/2009 | Higashi |
| 2009/0320756 A1 | 12/2009 | Tanaka |
| 2010/0000683 A1 | 1/2010 | Kadkhodayan et al. |
| 2010/0003824 A1 | 1/2010 | Kadkhodayan et al. |
| 2010/0006543 A1 | 1/2010 | Sawada et al. |
| 2010/0022030 A1 | 1/2010 | Ditizio |
| 2010/0025370 A1 | 2/2010 | Dieguez-Campo et al. |
| 2010/0039747 A1 | 2/2010 | Sansoni |
| 2010/0047080 A1 | 2/2010 | Bruce |

(56) References Cited

U.S. PATENT DOCUMENTS

| | | |
|---|---|---|
| 2010/0048027 A1 | 2/2010 | Cheng et al. |
| 2010/0055408 A1 | 3/2010 | Lee et al. |
| 2010/0055917 A1 | 3/2010 | Kim |
| 2010/0059889 A1 | 3/2010 | Gosset et al. |
| 2010/0062603 A1 | 3/2010 | Ganguly et al. |
| 2010/0075503 A1 | 3/2010 | Bencher et al. |
| 2010/0081285 A1 | 4/2010 | Chen et al. |
| 2010/0093151 A1 | 4/2010 | Arghavani et al. |
| 2010/0093168 A1 | 4/2010 | Naik |
| 2010/0096367 A1 | 4/2010 | Jeon et al. |
| 2010/0099236 A1 | 4/2010 | Kwon et al. |
| 2010/0099263 A1 | 4/2010 | Kao et al. |
| 2010/0101727 A1 | 4/2010 | Ji |
| 2010/0105209 A1 | 4/2010 | Winniczek et al. |
| 2010/0116788 A1 | 5/2010 | Singh et al. |
| 2010/0119843 A1 | 5/2010 | Sun et al. |
| 2010/0129974 A1 | 5/2010 | Futase et al. |
| 2010/0130001 A1 | 5/2010 | Noguchi |
| 2010/0139889 A1 | 6/2010 | Kurita et al. |
| 2010/0144140 A1 | 6/2010 | Chandrashekar et al. |
| 2010/0147219 A1 | 6/2010 | Hsieh et al. |
| 2010/0151149 A1 | 6/2010 | Ovshinsky |
| 2010/0164422 A1 | 7/2010 | Shu et al. |
| 2010/0173499 A1 | 7/2010 | Tao et al. |
| 2010/0178748 A1 | 7/2010 | Subramanian |
| 2010/0178755 A1 | 7/2010 | Lee et al. |
| 2010/0180819 A1 | 7/2010 | Hatanaka et al. |
| 2010/0183825 A1 | 7/2010 | Becker et al. |
| 2010/0187534 A1 | 7/2010 | Nishi et al. |
| 2010/0187588 A1 | 7/2010 | Kim et al. |
| 2010/0187694 A1 | 7/2010 | Yu et al. |
| 2010/0190352 A1 | 7/2010 | Jaiswal |
| 2010/0197143 A1 | 8/2010 | Nishimura |
| 2010/0203739 A1 | 8/2010 | Becker et al. |
| 2010/0207205 A1 | 8/2010 | Grebs et al. |
| 2010/0224324 A1 | 9/2010 | Kasai |
| 2010/0240205 A1 | 9/2010 | Son |
| 2010/0243165 A1 | 9/2010 | Um |
| 2010/0243606 A1 | 9/2010 | Koshimizu |
| 2010/0244204 A1 | 9/2010 | Matsuoka et al. |
| 2010/0252068 A1 | 10/2010 | Kannan et al. |
| 2010/0258913 A1 | 10/2010 | Lue |
| 2010/0267224 A1 | 10/2010 | Choi et al. |
| 2010/0267248 A1 | 10/2010 | Ma et al. |
| 2010/0273290 A1 | 10/2010 | Kryliouk |
| 2010/0273291 A1 | 10/2010 | Kryliouk et al. |
| 2010/0288369 A1 | 11/2010 | Chang et al. |
| 2010/0294199 A1 | 11/2010 | Tran et al. |
| 2010/0310785 A1 | 12/2010 | Sasakawa et al. |
| 2010/0314005 A1 | 12/2010 | Saito et al. |
| 2010/0330814 A1 | 12/2010 | Yokota et al. |
| 2011/0005607 A1 | 1/2011 | Desbiolles et al. |
| 2011/0005684 A1 | 1/2011 | Hayami et al. |
| 2011/0008950 A1 | 1/2011 | Xu |
| 2011/0011338 A1 | 1/2011 | Chuc et al. |
| 2011/0034035 A1 | 2/2011 | Liang et al. |
| 2011/0039407 A1 | 2/2011 | Nishizuka |
| 2011/0042799 A1 | 2/2011 | Kim et al. |
| 2011/0045676 A1 | 2/2011 | Park |
| 2011/0048325 A1 | 3/2011 | Choi et al. |
| 2011/0053380 A1 | 3/2011 | Sapre et al. |
| 2011/0058303 A1 | 3/2011 | Migita |
| 2011/0061810 A1 | 3/2011 | Ganguly et al. |
| 2011/0061812 A1 | 3/2011 | Ganguly et al. |
| 2011/0065276 A1 | 3/2011 | Ganguly et al. |
| 2011/0076401 A1 | 3/2011 | Chao et al. |
| 2011/0081782 A1 | 4/2011 | Liang et al. |
| 2011/0100489 A1 | 5/2011 | Orito |
| 2011/0104393 A1 | 5/2011 | Hilkene et al. |
| 2011/0111596 A1 | 5/2011 | Kanakasabapathy |
| 2011/0114601 A1 | 5/2011 | Lubomirsky et al. |
| 2011/0115378 A1 | 5/2011 | Lubomirsky et al. |
| 2011/0124144 A1 | 5/2011 | Schlemm et al. |
| 2011/0127156 A1 | 6/2011 | Foad et al. |
| 2011/0133650 A1 | 6/2011 | Kim |
| 2011/0140229 A1 | 6/2011 | Rachmady et al. |
| 2011/0143542 A1 | 6/2011 | Feurprier et al. |
| 2011/0146909 A1 | 6/2011 | Shi et al. |
| 2011/0147363 A1 | 6/2011 | Yap et al. |
| 2011/0151674 A1 | 6/2011 | Tang et al. |
| 2011/0151677 A1 | 6/2011 | Wang et al. |
| 2011/0151678 A1 | 6/2011 | Ashtiani et al. |
| 2011/0155181 A1 | 6/2011 | Inatomi |
| 2011/0159690 A1 | 6/2011 | Chandrashekar et al. |
| 2011/0165057 A1 | 7/2011 | Honda et al. |
| 2011/0165347 A1 | 7/2011 | Miller et al. |
| 2011/0165771 A1 | 7/2011 | Ring et al. |
| 2011/0174778 A1 | 7/2011 | Sawada et al. |
| 2011/0180847 A1 | 7/2011 | Ikeda et al. |
| 2011/0195575 A1 | 8/2011 | Wang |
| 2011/0198034 A1 | 8/2011 | Sun et al. |
| 2011/0204025 A1 | 8/2011 | Tahara |
| 2011/0207332 A1 | 8/2011 | Liu et al. |
| 2011/0217851 A1 | 9/2011 | Liang et al. |
| 2011/0226734 A1 | 9/2011 | Sumiya et al. |
| 2011/0227028 A1 | 9/2011 | Sekar et al. |
| 2011/0230008 A1 | 9/2011 | Lakshmanan et al. |
| 2011/0230052 A1 | 9/2011 | Tang et al. |
| 2011/0232737 A1 | 9/2011 | Ruletzki et al. |
| 2011/0232845 A1 | 9/2011 | Riker et al. |
| 2011/0244693 A1 | 10/2011 | Tamura et al. |
| 2011/0256421 A1 | 10/2011 | Bose et al. |
| 2011/0265884 A1 | 11/2011 | Xu et al. |
| 2011/0265951 A1 | 11/2011 | Xu |
| 2011/0266252 A1 | 11/2011 | Thadani et al. |
| 2011/0266256 A1 | 11/2011 | Cruse et al. |
| 2011/0266682 A1 | 11/2011 | Edelstein et al. |
| 2011/0278260 A1 | 11/2011 | Lai et al. |
| 2011/0287633 A1 | 11/2011 | Lee et al. |
| 2011/0294300 A1 | 12/2011 | Zhang et al. |
| 2011/0298061 A1 | 12/2011 | Siddiqui et al. |
| 2011/0304078 A1 | 12/2011 | Lee et al. |
| 2012/0003782 A1 | 1/2012 | Byun et al. |
| 2012/0009796 A1 | 1/2012 | Cui et al. |
| 2012/0025289 A1 | 2/2012 | Liang et al. |
| 2012/0031559 A1 | 2/2012 | Dhindsa et al. |
| 2012/0034786 A1 | 2/2012 | Dhindsa et al. |
| 2012/0035766 A1 | 2/2012 | Shajii et al. |
| 2012/0037596 A1 | 2/2012 | Eto et al. |
| 2012/0040492 A1 | 2/2012 | Ovshinsky et al. |
| 2012/0052683 A1 | 3/2012 | Kim et al. |
| 2012/0055402 A1 | 3/2012 | Moriya et al. |
| 2012/0068242 A1 | 3/2012 | Shin et al. |
| 2012/0070982 A1 | 3/2012 | Yu et al. |
| 2012/0070996 A1 | 3/2012 | Hao et al. |
| 2012/0091108 A1 | 4/2012 | Lin et al. |
| 2012/0097330 A1 | 4/2012 | Iyengar et al. |
| 2012/0103518 A1 | 5/2012 | Kakimoto |
| 2012/0104564 A1 | 5/2012 | Won et al. |
| 2012/0119225 A1 | 5/2012 | Shiomi et al. |
| 2012/0122319 A1 | 5/2012 | Shimizu |
| 2012/0129354 A1 | 5/2012 | Luong |
| 2012/0135576 A1 | 5/2012 | Lee et al. |
| 2012/0148369 A1 | 6/2012 | Michalski et al. |
| 2012/0149200 A1 | 6/2012 | Culp et al. |
| 2012/0161405 A1 | 6/2012 | Mohn et al. |
| 2012/0164839 A1 | 6/2012 | Nishimura |
| 2012/0171852 A1 | 7/2012 | Yuan et al. |
| 2012/0180954 A1 | 7/2012 | Yang et al. |
| 2012/0181599 A1 | 7/2012 | Lung |
| 2012/0182808 A1 | 7/2012 | Lue et al. |
| 2012/0196447 A1 | 8/2012 | Yang et al. |
| 2012/0196451 A1 | 8/2012 | Mallick |
| 2012/0202408 A1 | 8/2012 | Shajii et al. |
| 2012/0208361 A1 | 8/2012 | Ha |
| 2012/0211462 A1 | 8/2012 | Zhang et al. |
| 2012/0211722 A1 | 8/2012 | Kellam et al. |
| 2012/0222815 A1 | 9/2012 | Sabri et al. |
| 2012/0223048 A1 | 9/2012 | Paranjpe et al. |
| 2012/0223418 A1 | 9/2012 | Stowers et al. |
| 2012/0225557 A1 | 9/2012 | Serry et al. |
| 2012/0228642 A1 | 9/2012 | Aube et al. |
| 2012/0238102 A1 | 9/2012 | Zhang et al. |
| 2012/0238103 A1 | 9/2012 | Zhang et al. |

(56) References Cited

U.S. PATENT DOCUMENTS

| | | |
|---|---|---|
| 2012/0238108 A1 | 9/2012 | Chen et al. |
| 2012/0241411 A1 | 9/2012 | Darling et al. |
| 2012/0247390 A1 | 10/2012 | Sawada et al. |
| 2012/0247670 A1 | 10/2012 | Dobashi et al. |
| 2012/0247671 A1 | 10/2012 | Sugawara |
| 2012/0247677 A1 | 10/2012 | Himori et al. |
| 2012/0255491 A1 | 10/2012 | Hadidi |
| 2012/0258600 A1 | 10/2012 | Godet et al. |
| 2012/0267346 A1 | 10/2012 | Kao et al. |
| 2012/0269968 A1 | 10/2012 | Rayner |
| 2012/0282779 A1 | 11/2012 | Arnold et al. |
| 2012/0285619 A1 | 11/2012 | Matyushkin et al. |
| 2012/0285621 A1 | 11/2012 | Tan |
| 2012/0291696 A1 | 11/2012 | Clarke |
| 2012/0292664 A1 | 11/2012 | Kanike |
| 2012/0304933 A1 | 12/2012 | Mai et al. |
| 2012/0309204 A1 | 12/2012 | Kang et al. |
| 2012/0309205 A1 | 12/2012 | Wang et al. |
| 2012/0322015 A1 | 12/2012 | Kim |
| 2013/0001899 A1 | 1/2013 | Hwang et al. |
| 2013/0005103 A1 | 1/2013 | Liu et al. |
| 2013/0005140 A1 | 1/2013 | Jeng et al. |
| 2013/0012030 A1 | 1/2013 | Lakshmanan et al. |
| 2013/0012032 A1 | 1/2013 | Liu et al. |
| 2013/0023062 A1 | 1/2013 | Masuda et al. |
| 2013/0023124 A1 | 1/2013 | Nemani et al. |
| 2013/0026135 A1 | 1/2013 | Kim |
| 2013/0032574 A1 | 2/2013 | Liu et al. |
| 2013/0034666 A1 | 2/2013 | Liang et al. |
| 2013/0034968 A1 | 2/2013 | Zhang et al. |
| 2013/0037919 A1 | 2/2013 | Sapra et al. |
| 2013/0045605 A1 | 2/2013 | Wang et al. |
| 2013/0052804 A1 | 2/2013 | Song |
| 2013/0052827 A1 | 2/2013 | Wang et al. |
| 2013/0052833 A1 | 2/2013 | Ranjan et al. |
| 2013/0059440 A1 | 3/2013 | Wang et al. |
| 2013/0062675 A1 | 3/2013 | Thomas |
| 2013/0065398 A1 | 3/2013 | Ohsawa et al. |
| 2013/0082197 A1 | 4/2013 | Yang et al. |
| 2013/0084654 A1 | 4/2013 | Gaylord et al. |
| 2013/0087309 A1 | 4/2013 | Volfovski |
| 2013/0089988 A1 | 4/2013 | Wang et al. |
| 2013/0098868 A1 | 4/2013 | Nishimura et al. |
| 2013/0105303 A1 | 5/2013 | Lubomirsky et al. |
| 2013/0105948 A1 | 5/2013 | Kewley |
| 2013/0115372 A1 | 5/2013 | Pavol et al. |
| 2013/0118686 A1 | 5/2013 | Carducci et al. |
| 2013/0119016 A1 | 5/2013 | Kagoshima |
| 2013/0119457 A1 | 5/2013 | Lue et al. |
| 2013/0119483 A1 | 5/2013 | Alptekin et al. |
| 2013/0130507 A1 | 5/2013 | Wang et al. |
| 2013/0150303 A1 | 6/2013 | Kungl et al. |
| 2013/0155568 A1 | 6/2013 | Todorow et al. |
| 2013/0161726 A1 | 6/2013 | Kim et al. |
| 2013/0171810 A1 | 7/2013 | Sun et al. |
| 2013/0175654 A1 | 7/2013 | Muckenhirn et al. |
| 2013/0187220 A1 | 7/2013 | Surthi |
| 2013/0193108 A1 | 8/2013 | Zheng |
| 2013/0213935 A1 | 8/2013 | Liao et al. |
| 2013/0217243 A1 | 8/2013 | Underwood et al. |
| 2013/0224953 A1 | 8/2013 | Salinas et al. |
| 2013/0224960 A1 | 8/2013 | Payyapilly et al. |
| 2013/0260533 A1 | 10/2013 | Sapre et al. |
| 2013/0260564 A1 | 10/2013 | Sapre et al. |
| 2013/0279066 A1 | 10/2013 | Lubomirsky et al. |
| 2013/0284369 A1 | 10/2013 | Kobayashi et al. |
| 2013/0284370 A1 | 10/2013 | Kobayashi et al. |
| 2013/0284373 A1 | 10/2013 | Sun et al. |
| 2013/0284374 A1 | 10/2013 | Lubomirsky et al. |
| 2013/0286530 A1 | 10/2013 | Lin et al. |
| 2013/0295297 A1 | 11/2013 | Chou et al. |
| 2013/0298942 A1 | 11/2013 | Ren et al. |
| 2013/0302980 A1 | 11/2013 | Chandrashekar et al. |
| 2013/0337655 A1 | 12/2013 | Lee et al. |
| 2013/0343829 A1 | 12/2013 | Benedetti et al. |
| 2014/0004707 A1 | 1/2014 | Thedjoisworo et al. |
| 2014/0004708 A1 | 1/2014 | Thedjoisworo |
| 2014/0008880 A1 | 1/2014 | Miura et al. |
| 2014/0020708 A1 | 1/2014 | Kim et al. |
| 2014/0021673 A1 | 1/2014 | Chen et al. |
| 2014/0026813 A1 | 1/2014 | Wang et al. |
| 2014/0053866 A1 | 2/2014 | Baluja et al. |
| 2014/0057447 A1 | 2/2014 | Yang et al. |
| 2014/0062285 A1 | 3/2014 | Chen |
| 2014/0065827 A1 | 3/2014 | Kang et al. |
| 2014/0065842 A1 | 3/2014 | Anthis et al. |
| 2014/0080308 A1 | 3/2014 | Chen et al. |
| 2014/0080309 A1 | 3/2014 | Park |
| 2014/0080310 A1 | 3/2014 | Chen et al. |
| 2014/0083362 A1 | 3/2014 | Lubomirsky et al. |
| 2014/0087488 A1 | 3/2014 | Nam et al. |
| 2014/0097270 A1 | 4/2014 | Liang et al. |
| 2014/0099794 A1 | 4/2014 | Ingle et al. |
| 2014/0102367 A1 | 4/2014 | Ishibashi |
| 2014/0124364 A1 | 5/2014 | Yoo et al. |
| 2014/0134842 A1 | 5/2014 | Zhang et al. |
| 2014/0134847 A1 | 5/2014 | Seya |
| 2014/0141621 A1 | 5/2014 | Ren et al. |
| 2014/0147126 A1 | 5/2014 | Yamashita et al. |
| 2014/0152312 A1 | 6/2014 | Snow et al. |
| 2014/0154668 A1 | 6/2014 | Chou et al. |
| 2014/0154889 A1 | 6/2014 | Wang et al. |
| 2014/0165912 A1 | 6/2014 | Kao et al. |
| 2014/0166617 A1 | 6/2014 | Chen |
| 2014/0166618 A1 | 6/2014 | Tadigadapa et al. |
| 2014/0186772 A1 | 7/2014 | Pohlers et al. |
| 2014/0190410 A1 | 7/2014 | Kim |
| 2014/0191388 A1 | 7/2014 | Chen |
| 2014/0199850 A1 | 7/2014 | Kim et al. |
| 2014/0199851 A1 | 7/2014 | Nemani et al. |
| 2014/0209245 A1 | 7/2014 | Yamamoto et al. |
| 2014/0216337 A1 | 8/2014 | Swaminathan et al. |
| 2014/0225504 A1 | 8/2014 | Kaneko et al. |
| 2014/0227881 A1 | 8/2014 | Lubomirsky et al. |
| 2014/0234466 A1 | 8/2014 | Gao et al. |
| 2014/0248773 A1 | 9/2014 | Tsai et al. |
| 2014/0248780 A1 | 9/2014 | Ingle et al. |
| 2014/0256131 A1 | 9/2014 | Wang et al. |
| 2014/0256145 A1 | 9/2014 | Abdallah et al. |
| 2014/0262031 A1 | 9/2014 | Belostotskiy et al. |
| 2014/0262038 A1 | 9/2014 | Wang et al. |
| 2014/0263172 A1 | 9/2014 | Xie et al. |
| 2014/0263272 A1 | 9/2014 | Duan et al. |
| 2014/0264507 A1 | 9/2014 | Lee et al. |
| 2014/0264533 A1 | 9/2014 | Simsek-Ege |
| 2014/0271097 A1 | 9/2014 | Wang et al. |
| 2014/0273373 A1 | 9/2014 | Makala et al. |
| 2014/0273406 A1 | 9/2014 | Wang et al. |
| 2014/0273451 A1 | 9/2014 | Wang et al. |
| 2014/0273462 A1 | 9/2014 | Simsek-Ege et al. |
| 2014/0273487 A1 | 9/2014 | Deshmukh et al. |
| 2014/0273489 A1 | 9/2014 | Wang et al. |
| 2014/0273491 A1 | 9/2014 | Zhang et al. |
| 2014/0273492 A1 | 9/2014 | Anthis et al. |
| 2014/0273496 A1 | 9/2014 | Kao |
| 2014/0288528 A1 | 9/2014 | Py et al. |
| 2014/0302678 A1 | 10/2014 | Paterson et al. |
| 2014/0302680 A1 | 10/2014 | Singh |
| 2014/0308758 A1 | 10/2014 | Nemani et al. |
| 2014/0308816 A1 | 10/2014 | Wang et al. |
| 2014/0311581 A1 | 10/2014 | Belostotskiy et al. |
| 2014/0342532 A1 | 11/2014 | Zhu |
| 2014/0342569 A1 | 11/2014 | Zhu et al. |
| 2014/0349477 A1 | 11/2014 | Chandrashekar et al. |
| 2014/0357083 A1 | 12/2014 | Ling et al. |
| 2014/0361684 A1 | 12/2014 | Ikeda et al. |
| 2014/0363979 A1 | 12/2014 | Or et al. |
| 2015/0011096 A1 | 1/2015 | Chandrasekharan et al. |
| 2015/0014152 A1 | 1/2015 | Hoinkis et al. |
| 2015/0031211 A1 | 1/2015 | Sapre et al. |
| 2015/0037980 A1 | 2/2015 | Rha |
| 2015/0041430 A1 | 2/2015 | Yoshino et al. |
| 2015/0050812 A1 | 2/2015 | Smith |
| 2015/0060265 A1 | 3/2015 | Cho et al. |

(56) References Cited

U.S. PATENT DOCUMENTS

| | | |
|---|---|---|
| 2015/0064918 A1 | 3/2015 | Ranjan et al. |
| 2015/0072508 A1 | 3/2015 | Or et al. |
| 2015/0076110 A1 | 3/2015 | Wu et al. |
| 2015/0076586 A1 | 3/2015 | Rabkin et al. |
| 2015/0079797 A1 | 3/2015 | Chen et al. |
| 2015/0093891 A1 | 4/2015 | Zope |
| 2015/0118858 A1 | 4/2015 | Takaba |
| 2015/0126035 A1 | 5/2015 | Diao et al. |
| 2015/0126039 A1 | 5/2015 | Korolik et al. |
| 2015/0126040 A1 | 5/2015 | Korolik et al. |
| 2015/0129541 A1 | 5/2015 | Wang et al. |
| 2015/0129545 A1 | 5/2015 | Ingle et al. |
| 2015/0129546 A1 | 5/2015 | Ingle et al. |
| 2015/0132953 A1 | 5/2015 | Nowling |
| 2015/0132968 A1 | 5/2015 | Ren et al. |
| 2015/0152072 A1 | 6/2015 | Cantat et al. |
| 2015/0155177 A1* | 6/2015 | Zhang ................. H01L 21/3065 438/719 |
| 2015/0170879 A1 | 6/2015 | Nguyen et al. |
| 2015/0170920 A1 | 6/2015 | Purayath et al. |
| 2015/0170924 A1 | 6/2015 | Nguyen et al. |
| 2015/0170926 A1 | 6/2015 | Michalak |
| 2015/0170935 A1 | 6/2015 | Wang et al. |
| 2015/0170943 A1 | 6/2015 | Nguyen et al. |
| 2015/0171008 A1 | 6/2015 | Luo |
| 2015/0179464 A1 | 6/2015 | Wang et al. |
| 2015/0187625 A1 | 7/2015 | Busche et al. |
| 2015/0200042 A1 | 7/2015 | Ling et al. |
| 2015/0206764 A1 | 7/2015 | Wang et al. |
| 2015/0214066 A1 | 7/2015 | Luere et al. |
| 2015/0214067 A1 | 7/2015 | Zhang et al. |
| 2015/0214092 A1 | 7/2015 | Purayath et al. |
| 2015/0214337 A1 | 7/2015 | Ko et al. |
| 2015/0221479 A1 | 8/2015 | Chen et al. |
| 2015/0221541 A1 | 8/2015 | Nemani et al. |
| 2015/0228456 A1 | 8/2015 | Ye et al. |
| 2015/0235809 A1 | 8/2015 | Ito et al. |
| 2015/0235860 A1 | 8/2015 | Tomura et al. |
| 2015/0235863 A1 | 8/2015 | Chen |
| 2015/0235865 A1 | 8/2015 | Wang et al. |
| 2015/0235867 A1 | 8/2015 | Nishizuka |
| 2015/0247231 A1 | 9/2015 | Nguyen et al. |
| 2015/0249018 A1 | 9/2015 | Park et al. |
| 2015/0270140 A1 | 9/2015 | Gupta et al. |
| 2015/0275361 A1 | 10/2015 | Lubomirsky et al. |
| 2015/0275375 A1 | 10/2015 | Kim et al. |
| 2015/0279687 A1 | 10/2015 | Xue et al. |
| 2015/0294980 A1 | 10/2015 | Lee et al. |
| 2015/0332930 A1 | 11/2015 | Wang et al. |
| 2015/0340225 A1 | 11/2015 | Kim et al. |
| 2015/0345029 A1 | 12/2015 | Wang et al. |
| 2015/0357201 A1 | 12/2015 | Chen et al. |
| 2015/0357205 A1 | 12/2015 | Wang et al. |
| 2015/0371861 A1 | 12/2015 | Li et al. |
| 2015/0371864 A1 | 12/2015 | Hsu et al. |
| 2015/0371865 A1 | 12/2015 | Chen et al. |
| 2015/0371866 A1 | 12/2015 | Chen et al. |
| 2015/0380431 A1 | 12/2015 | Kanamori et al. |
| 2016/0005572 A1 | 1/2016 | Liang et al. |
| 2016/0005833 A1 | 1/2016 | Collins et al. |
| 2016/0027654 A1 | 1/2016 | Kim et al. |
| 2016/0027673 A1 | 1/2016 | Wang et al. |
| 2016/0035586 A1 | 2/2016 | Purayath et al. |
| 2016/0035614 A1 | 2/2016 | Purayath et al. |
| 2016/0042968 A1 | 2/2016 | Purayath et al. |
| 2016/0043099 A1 | 2/2016 | Purayath et al. |
| 2016/0056167 A1 | 2/2016 | Wang et al. |
| 2016/0064212 A1 | 3/2016 | Thedjoisworo et al. |
| 2016/0064233 A1 | 3/2016 | Wang et al. |
| 2016/0079072 A1 | 3/2016 | Wang et al. |
| 2016/0086772 A1 | 3/2016 | Khaja |
| 2016/0086807 A1 | 3/2016 | Park et al. |
| 2016/0086808 A1 | 3/2016 | Zhang et al. |
| 2016/0086815 A1 | 3/2016 | Pandit et al. |
| 2016/0086816 A1* | 3/2016 | Wang ................. H01L 21/31122 438/694 |
| 2016/0093505 A1 | 3/2016 | Chen et al. |
| 2016/0093506 A1 | 3/2016 | Chen et al. |
| 2016/0093737 A1 | 3/2016 | Li et al. |
| 2016/0104606 A1 | 4/2016 | Park et al. |
| 2016/0109863 A1 | 4/2016 | Valcore et al. |
| 2016/0117425 A1 | 4/2016 | Povolny et al. |
| 2016/0118227 A1 | 4/2016 | Valcore et al. |
| 2016/0118268 A1 | 4/2016 | Ingle et al. |
| 2016/0118396 A1 | 4/2016 | Rabkin et al. |
| 2016/0126118 A1 | 5/2016 | Chen et al. |
| 2016/0133480 A1 | 5/2016 | Ko et al. |
| 2016/0148805 A1 | 5/2016 | Jongbloed et al. |
| 2016/0148821 A1 | 5/2016 | Singh et al. |
| 2016/0163512 A1 | 6/2016 | Lubomirsky |
| 2016/0163513 A1 | 6/2016 | Lubomirsky |
| 2016/0172216 A1 | 6/2016 | Marakhtanov et al. |
| 2016/0181112 A1 | 6/2016 | Xue et al. |
| 2016/0181116 A1 | 6/2016 | Berry et al. |
| 2016/0189933 A1 | 6/2016 | Kobayashi et al. |
| 2016/0196969 A1 | 7/2016 | Berry et al. |
| 2016/0196984 A1 | 7/2016 | Lill et al. |
| 2016/0196985 A1 | 7/2016 | Tan et al. |
| 2016/0204009 A1 | 7/2016 | Nguyen et al. |
| 2016/0218018 A1 | 7/2016 | Liu et al. |
| 2016/0222522 A1 | 8/2016 | Wang et al. |
| 2016/0225651 A1 | 8/2016 | Tran et al. |
| 2016/0225652 A1 | 8/2016 | Tran et al. |
| 2016/0237570 A1 | 8/2016 | Tan et al. |
| 2016/0240389 A1 | 8/2016 | Zhang et al. |
| 2016/0240402 A1 | 8/2016 | Park et al. |
| 2016/0260588 A1 | 9/2016 | Park et al. |
| 2016/0260616 A1 | 9/2016 | Li et al. |
| 2016/0260619 A1 | 9/2016 | Zhang et al. |
| 2016/0284556 A1 | 9/2016 | Ingle et al. |
| 2016/0293438 A1 | 10/2016 | Zhou et al. |
| 2016/0300694 A1 | 10/2016 | Yang et al. |
| 2016/0307772 A1 | 10/2016 | Choi et al. |
| 2016/0307773 A1 | 10/2016 | Lee et al. |
| 2016/0314961 A1 | 10/2016 | Liu et al. |
| 2016/0314985 A1 | 10/2016 | Yang et al. |
| 2016/0319452 A1 | 11/2016 | Eidschun et al. |
| 2016/0343548 A1 | 11/2016 | Howald et al. |
| 2017/0040175 A1 | 2/2017 | Xu et al. |
| 2017/0040190 A1 | 2/2017 | Benjaminson et al. |
| 2017/0040191 A1 | 2/2017 | Benjaminson et al. |
| 2017/0040207 A1 | 2/2017 | Purayath |
| 2017/0040214 A1 | 2/2017 | Lai et al. |
| 2017/0062184 A1 | 3/2017 | Tran et al. |
| 2017/0110290 A1 | 4/2017 | Kobayashi et al. |
| 2017/0110335 A1 | 4/2017 | Yang et al. |
| 2017/0110475 A1 | 4/2017 | Liu et al. |
| 2017/0133202 A1 | 5/2017 | Berry |
| 2017/0178894 A1 | 6/2017 | Stone et al. |
| 2017/0178924 A1 | 6/2017 | Chen et al. |
| 2017/0207088 A1 | 7/2017 | Kwon et al. |
| 2017/0226637 A1 | 8/2017 | Lubomirsky et al. |
| 2017/0229287 A1 | 8/2017 | Xu et al. |
| 2017/0229289 A1 | 8/2017 | Lubomirsky et al. |
| 2017/0229291 A1 | 8/2017 | Singh et al. |
| 2017/0229293 A1 | 8/2017 | Park et al. |
| 2017/0229326 A1 | 8/2017 | Tran et al. |
| 2017/0229328 A1 | 8/2017 | Benjaminson et al. |
| 2017/0229329 A1 | 8/2017 | Benjaminson et al. |
| 2017/0236694 A1 | 8/2017 | Eason et al. |
| 2017/0309509 A1 | 10/2017 | Tran et al. |
| 2017/0338133 A1 | 11/2017 | Tan et al. |
| 2017/0338134 A1 | 11/2017 | Tan et al. |
| 2018/0005850 A1 | 1/2018 | Citla et al. |
| 2018/0025900 A1 | 1/2018 | Park et al. |
| 2018/0076031 A1 | 3/2018 | Yan et al. |
| 2018/0076044 A1 | 3/2018 | Choi et al. |
| 2018/0076083 A1 | 3/2018 | Ko et al. |
| 2018/0082861 A1 | 3/2018 | Citla et al. |
| 2018/0096818 A1 | 4/2018 | Lubomirsky |
| 2018/0096819 A1 | 4/2018 | Lubomirsky et al. |
| 2018/0096821 A1 | 4/2018 | Lubomirsky et al. |
| 2018/0096865 A1 | 4/2018 | Lubomirsky et al. |

(56) References Cited

U.S. PATENT DOCUMENTS

| | | |
|---|---|---|
| 2018/0102255 A1 | 4/2018 | Chen et al. |
| 2018/0102256 A1 | 4/2018 | Chen et al. |
| 2018/0102259 A1 | 4/2018 | Wang et al. |
| 2018/0138049 A1 | 5/2018 | Ko et al. |
| 2018/0138055 A1 | 5/2018 | Xu et al. |
| 2018/0138075 A1 | 5/2018 | Kang et al. |
| 2018/0138085 A1 | 5/2018 | Wang et al. |
| 2018/0182633 A1 | 6/2018 | Pandit et al. |
| 2018/0226223 A1 | 8/2018 | Lubomirsky |
| 2018/0226230 A1 | 8/2018 | Kobayashi et al. |
| 2018/0226259 A1 | 8/2018 | Choi et al. |
| 2018/0226278 A1 | 8/2018 | Arnepalli et al. |
| 2018/0226425 A1 | 8/2018 | Purayath |
| 2018/0226426 A1 | 8/2018 | Purayath |
| 2018/0261516 A1 | 9/2018 | Lin et al. |
| 2018/0261686 A1 | 9/2018 | Lin et al. |

FOREIGN PATENT DOCUMENTS

| | | |
|---|---|---|
| CN | 101236893 A | 8/2008 |
| CN | 101378850 A | 3/2009 |
| CN | 102893705 | 1/2013 |
| EP | 1675160 A1 | 6/2006 |
| JP | S59-126778 A | 7/1984 |
| JP | S62-45119 A | 2/1987 |
| JP | 63301051 A | 12/1988 |
| JP | H01-200627 A | 8/1989 |
| JP | H02-114525 A | 4/1990 |
| JP | H07-153739 A | 6/1995 |
| JP | H8-31755 A | 2/1996 |
| JP | H08-107101 A | 4/1996 |
| JP | H08-264510 A | 10/1996 |
| JP | H09-260356 A | 10/1997 |
| JP | 2001-313282 A | 11/2001 |
| JP | 2001-332608 A | 11/2001 |
| JP | 2002-075972 A | 3/2002 |
| JP | 2002-083869 A | 3/2002 |
| JP | 2003-174020 A | 6/2003 |
| JP | 2003-282591 A | 10/2003 |
| JP | 2004-508709 A | 3/2004 |
| JP | 2004-296467 A | 10/2004 |
| JP | 2005-050908 A | 2/2005 |
| JP | 2006-041039 A | 2/2006 |
| JP | 2006-066408 A | 3/2006 |
| JP | 2008-288560 A | 11/2008 |
| JP | 4191137 B2 | 12/2008 |
| JP | 2009-141343 A | 6/2009 |
| JP | 2009-530871 A | 8/2009 |
| JP | 2009-239056 A | 10/2009 |
| JP | 2010-180458 | 8/2010 |
| JP | 2011-508436 A | 3/2011 |
| JP | 2011-518408 A | 6/2011 |
| JP | 4763293 B2 | 8/2011 |
| JP | 2011-171378 A | 9/2011 |
| JP | 2012-19164 A | 1/2012 |
| JP | 2012-019194 A | 1/2012 |
| JP | 2012-512531 A | 5/2012 |
| JP | 2013-243418 A | 12/2013 |
| JP | 5802323 B2 | 10/2015 |
| JP | 2016-111177 A | 6/2016 |
| KR | 10-2000-008278 A | 2/2000 |
| KR | 10-2000-0064946 A | 11/2000 |
| KR | 10-2001-0056735 A | 7/2001 |
| KR | 2003-0023964 A | 3/2003 |
| KR | 10-2003-0054726 A | 7/2003 |
| KR | 10-2003-0083663 A | 10/2003 |
| KR | 100441297 B1 | 7/2004 |
| KR | 10-2005-0007143 A | 1/2005 |
| KR | 10-2005-0042701 A | 5/2005 |
| KR | 2005-0049903 A | 5/2005 |
| KR | 10-2006-0080509 A | 7/2006 |
| KR | 1006-41762 B1 | 11/2006 |
| KR | 10-2006-0127173 A | 12/2006 |
| KR | 100663668 B1 | 1/2007 |
| KR | 100678696 B1 | 1/2007 |
| KR | 100712727 B1 | 4/2007 |
| KR | 2007-0079870 A | 8/2007 |
| KR | 10-2008-0063988 A | 7/2008 |
| KR | 10-0843236 B1 | 7/2008 |
| KR | 10-2009-0040869 A | 11/2009 |
| KR | 10-2009-0128913 A | 12/2009 |
| KR | 10-2010-0013980 A | 2/2010 |
| KR | 10-2010-0093358 A | 8/2010 |
| KR | 10-2011-0086540 A | 7/2011 |
| KR | 10-2011-0114538 A | 10/2011 |
| KR | 10-2011-0126675 A | 11/2011 |
| KR | 10-2012-0022251 A | 3/2012 |
| KR | 10-2012-0082640 A | 7/2012 |
| KR | 10-2016-0002543 A | 1/2016 |
| TW | 2006-12480 A | 4/2006 |
| TW | 200709256 A | 3/2007 |
| TW | 2007-35196 A | 9/2007 |
| TW | 2011-27983 A1 | 8/2011 |
| TW | 2012-07919 | 2/2012 |
| TW | 2012-13594 A | 4/2012 |
| TW | 2012-33842 A1 | 8/2012 |
| WO | 2008-112673 A2 | 9/2008 |
| WO | 2009-009611 A2 | 1/2009 |
| WO | 2009-084194 A1 | 7/2009 |
| WO | 2010-010706 | 1/2010 |
| WO | 2010-113946 A1 | 10/2010 |
| WO | 2011-027515 A | 3/2011 |
| WO | 2011-031556 A | 3/2011 |
| WO | 2011070945 A1 | 6/2011 |
| WO | 2011-095846 A1 | 8/2011 |
| WO | 2011-149638 A | 12/2011 |
| WO | 2012-050321 A | 4/2012 |
| WO | 2012-18987 A1 | 9/2012 |
| WO | 2012-125656 A2 | 9/2012 |
| WO | 2012-148568 A1 | 11/2012 |
| WO | 2013-118260 A1 | 8/2013 |

OTHER PUBLICATIONS

International Search Report and Written Opinion of PCT/US2017/060696 dated Jan. 25, 2018, all pages.

International Search Report and Written Opinion of PCT/US2017/055431 dated Jan. 19, 2018, all pages.

International Search Report and Written Opinion of PCT/US2017/047209 dated Nov. 24, 2017, all pages.

International Search Report and Written Opinion of PCT/US2017/033362 dated Aug. 24, 2017, all pages.

H. Xiao, Introduction to Semiconductor Manufacturing Technology, published by Prentice Hall, 2001, ISBN 0-13-022404-9, pp. 354-356.

Manual No. TQMA72E1. "Bayard-Alpert Pirani Gauge FRG-730: Short Operating Instructions" Mar. 2012. Agilent Technologies, Lexington, MA 02421, USA. pp. 1-45.

International Search Report and Written Opinion of PCT/US2016/045551 dated Nov. 17, 2016, all pages.

International Search Report and Written Opinion of PCT/US2016/045543 dated Nov. 17, 2016, all pages.

"Liang et al. Industrial Application of Plasma Process vol. 3, pp. 61-74, 2010".

Instrument Manual: Vacuum Gauge Model MM200, Rev D. TELEVAC (website: www.televac.com), A Division of the Fredericks Company, Huntingdon Valley, PA, US. 2008. pp. 162.

J.J. Wang and et al., "Inductively coupled plasma etching of bulk 1-20 6H-SiC and thin-film SiCN in NF3 chemistries," Journal of Vacuum Science & Technology A: Vacuum, Surfaces, and Films 16, 2204 (1998).

International Search Report and Written Opinion of PCT/US2018/016261 dated May 21, 2018, all pages.

International Search Report and Written Opinion of PCT/US2018/016648 dated May 18, 2018, all pages.

\* cited by examiner

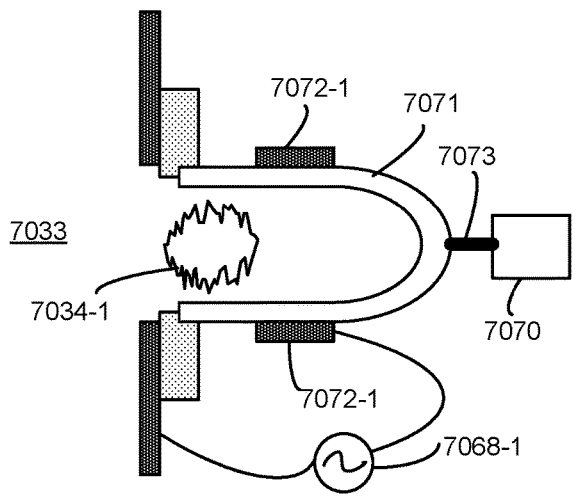
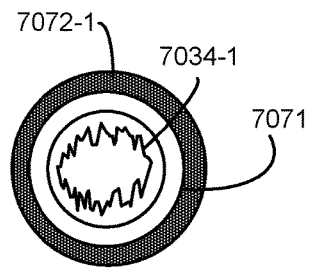
FIG. 7A
FIG. 7B
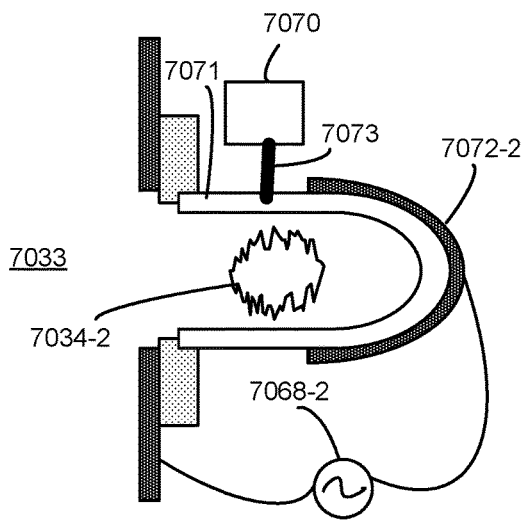
FIG. 7C

OPTICAL EMISSION SPECTROSCOPY (OES) FOR REMOTE PLASMA MONITORING

FIELD

Embodiments disclosed herein relate to remote plasma etch processes.

BACKGROUND

Integrated circuits are made possible by processes which produce intricately patterned material layers on substrate surfaces. Producing patterned material on a substrate requires controlled methods for removal of exposed material. Chemical etching is used for a variety of purposes including transferring a photoresist pattern into underlying layers, thinning layers or thinning lateral dimensions of features already present on the surface. Often it is desirable to have an etch process which etches one material faster than another helping e.g. a pattern transfer process proceed. Such an etch process is said to be selective of the first material relative to the second material. As a result of the diversity of materials, circuits and processes, etch processes have been developed with a selectivity towards a variety of materials.

Dry etch processes are often desirable for selectively removing material from semiconductor substrates. The desirability stems from the ability to gently remove material from miniature structures with minimal physical disturbance. Dry etch processes also allow the etch rate to be abruptly stopped by removing the gas phase reagents. Some dry-etch processes involve the exposure of a substrate to remote plasma by-products formed from one or more precursors. Remote excitation of etchants in a remote plasma system (instead of locally) may desirably increase selectivity.

Methods and systems are needed to monitor aspects of remote plasmas in-situ for a variety of purposes.

SUMMARY

Methods and systems for etching substrates using a remote plasma are described. Remotely excited etchants are formed in a remote plasma and flowed through a showerhead into a substrate processing region to etch the substrate. Optical emission spectra are acquired from the substrate processing region just above the substrate. The optical emission spectra may be used to determine an endpoint of the etch, determine the etch rate or otherwise characterize the etch process in-situ. A weak plasma may be present in the substrate processing region. The weak plasma may have lower intensity than the remote plasma. In cases where no bias plasma above the substrate is used in an etch process, a weak plasma may be ignited near a viewport disposed near the side of the substrate processing region to characterize the etchants.

Embodiments disclosed herein include methods of etching a substrate. The methods include placing the substrate in a substrate processing region of a substrate processing chamber. The methods further include flowing a fluorine-containing precursor into a remote plasma region separated from the substrate processing region by a showerhead. The methods further include forming a remote plasma having a remote plasma power in the remote plasma region. The methods further include producing plasma effluents from the fluorine-containing precursor in the remote plasma in the remote plasma region. The methods further include flowing the plasma effluents through the showerhead into the substrate processing region. The methods further include etching the substrate with the plasma effluents. The methods further include forming a local plasma having a local plasma power in the substrate processing region. The methods further include acquiring an optical emission spectrum through a viewport affixed to a side of the substrate processing chamber, the side forming a border of the substrate processing region. The optical emission spectrum represents intensity as a function of optical wavelength and the optical emission spectrum is acquired with an optical emission spectrometer.

The remote plasma power of the remote plasma may exceed the local plasma power of the local plasma by a factor of ten or more. The local plasma may be centered over the substrate. The local plasma may be positioned above the substrate and outside an edge of the substrate near the viewport. The local plasma may be formed using an electrode located on the outside of the viewport and the local plasma power may be applied between the electrode and the substrate processing chamber. The local plasma may be formed using a first electrode and a second electrode, each positioned on the outside of the viewport and the local plasma power may be applied between the first electrode and the second electrode.

Embodiments disclosed herein include substrate processing chambers The substrate processing chambers include a remote plasma region. The remote plasma region is configured to receive a fluorine-containing precursor and form a remote plasma from the fluorine-containing precursor. The substrate processing chambers further include a remote plasma power supply configured to apply a remote plasma power to the remote plasma region and configured to form the remote plasma. The substrate processing chambers further include a substrate processing region. The substrate processing chambers further include a showerhead positioned between the remote plasma region and the substrate processing region. The substrate processing region is fluidly coupled to the remote plasma region by through-holes in the showerhead. The substrate processing chambers further include a pedestal configured to support a substrate. The substrate processing chambers further include a flange attached to the substrate processing chamber. The flange forms a vacuum seal with the substrate processing chamber. The substrate processing chamber further includes a viewport attached to the flange forming a vacuum seal with the flange. The viewport is optically transmissive in a near infrared spectrum. The substrate processing chambers further include an optical emission spectrometer configured to receive optical radiation after the optical radiation passes through the viewport. The optical emission spectrometer is positioned on an exterior of the viewport and the optical radiation originates from inside the substrate processing region above the substrate.

The substrate processing chambers may further include a local plasma power supply configured to form a local plasma in the substrate processing region. The local plasma may have a local plasma power less than 10% of the remote plasma power. The substrate processing chambers may further include a fiber optic cable configured to guide the optical radiation from the viewport to the optical emission spectrometer. The substrate processing chambers may further include an electrode proximal to the viewport. The electrode may be positioned on the exterior of the viewport. The substrate processing chambers may further include a plasma power supply configured to apply a plasma power to the electrode. The substrate processing chambers may further include a second electrode configured to apply a plasma power to the electrode. The electrode may be electrically insulated from the second electrode.

Embodiments disclosed herein include optical emission spectrometer assemblies. The optical emission spectrometer assemblies include a flange configured to attach to a substrate processing chamber. The flange is configured to form a vacuum seal with the substrate processing chamber. The optical emission spectrometer assemblies further include a planar viewport attached to the flange forming a vacuum seal with the flange. The planar viewport is optically transmissive in a near infrared spectrum. The optical emission spectrometer assemblies further include an electrode proximal to the planar viewport. The electrode is disposed on an external side of the planar viewport. The optical emission spectrometer assemblies further include an optical emission spectrometer configured to receive optical radiation after the optical radiation passes through the planar viewport. The optical emission spectrometer is positioned on the external side of the planar viewport. The optical emission spectrometer assemblies further include a plasma power supply configured to apply a plasma power to the electrode.

The optical emission spectrometer assemblies may further include a fiber optic cable configured to guide infrared light from the planar viewport to the optical emission spectrometer. The plasma power supply may be configured to apply the plasma power between the electrode and the substrate processing chamber. The optical emission spectrometer assemblies may further include a second electrode proximal to the planar viewport. The electrode may be electrically insulated from the second electrode. The plasma power supply may be configured to apply the plasma power between the electrode and the second electrode.

Additional embodiments and features are set forth in part in the description that follows, and in part will become apparent to those skilled in the art upon examination of the specification or may be learned by the practice of the disclosed embodiments. The features and advantages of the disclosed embodiments may be realized and attained by means of the instrumentalities, combinations, and methods described in the specification.

DESCRIPTION OF THE DRAWINGS

A further understanding of the nature and advantages of the embodiments may be realized by reference to the remaining portions of the specification and the drawings.

FIG. 7A shows a cross-sectional side view of a weak plasma viewport according to embodiments.

FIG. 7B shows a cross-sectional end view of a weak plasma viewport according to embodiments.

FIG. 7C shows a cross-sectional side view of a weak plasma viewport according to embodiments.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Methods and systems for etching substrates using a remote plasma are described. Remotely excited etchants are formed in a remote plasma and flowed through a showerhead into a substrate processing region to etch the substrate. Optical emission spectra are acquired from the substrate processing region just above the substrate. The optical emission spectra may be used to determine an endpoint of the etch, determine the etch rate or otherwise characterize the etch process in-situ. A weak plasma may be present in the substrate processing region. The weak plasma may have much lower intensity than the remote plasma. In cases where no bias plasma above the substrate is used in an etch process, a weak plasma may be ignited near a viewport disposed near the side of the substrate processing region to characterize the etchants.

In the past, gas phase etch processes have excited $NF_3$ in a local plasma inside substrate processing region. Optical emission spectroscopy was performed by flowing some of the reactants in the substrate processing region through tubing to a separate plasma used for the characterization and then disposing any chemical effluents through a vacuum pump. Recently, high selectivity gas-phase etch processes have been developed using a spatially-constrained remote plasma region separated from the substrate processing region by a showerhead (sometimes a dual-channel showerhead). Plasma effluents are formed in the remote plasma region and flow into the substrate processing region through the showerhead. The remote plasma effluents are optionally further excited in a bias plasma above the substrate.

The methods and systems described herein provide the benefit of characterizing remote plasma etch processes in the substrate processing region where there is more space than in the remote plasma region. The characterization of the plasma effluents occurs closer to the substrate, providing a more accurate determination of the etch process compared to the more circuitous sampling routes used previously.

Figure 1:
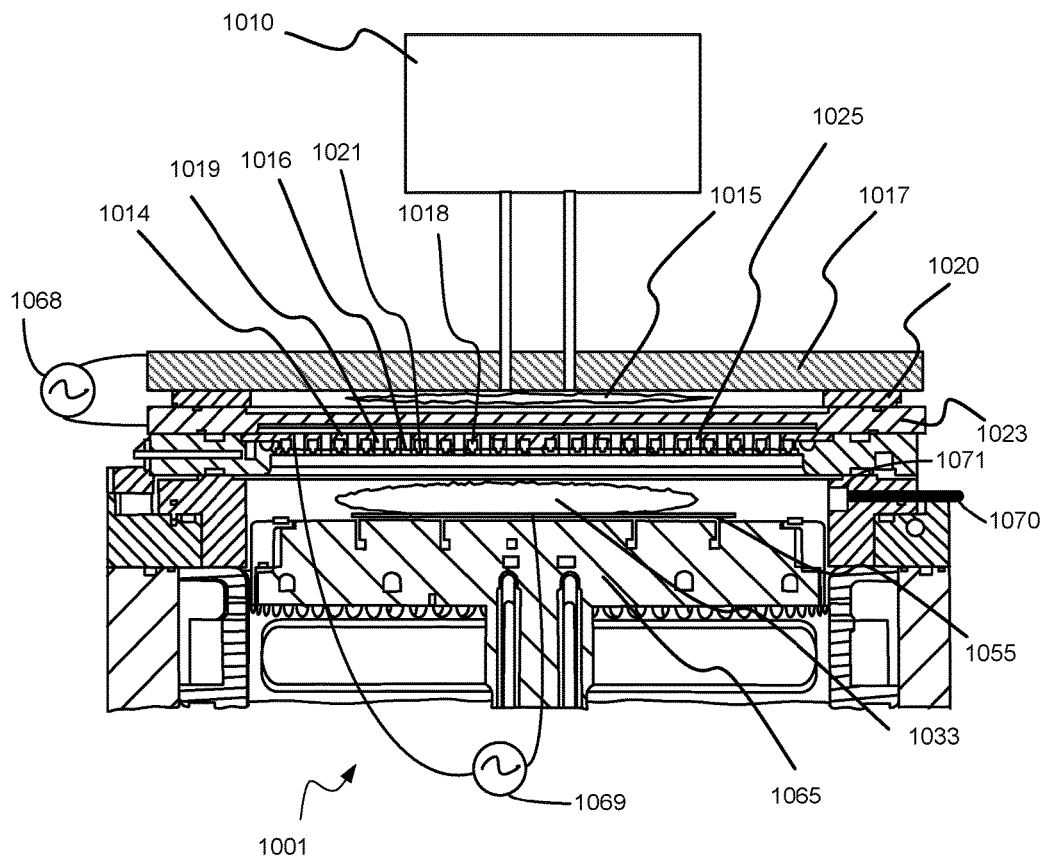
FIG. 1 shows a schematic cross-sectional view of a substrate processing chamber according to embodiments.

FIG. 1 shows a schematic cross-sectional view of an exemplary substrate processing chamber. The schematic of the substrate processing chamber 1001 serves to introduce the optical emission spectrometer but also provide context for alternative configurations and details provided in subsequent descriptions. Later drawings will provide less detail compared to FIG. 1 but only for the sake of brevity. Any combination of features found in FIG. 1 may be present in any or all subsequent embodiments. The substrate processing chamber 1001 has a remote plasma region 1015 and a substrate processing region 1033 inside. The remote plasma region 1015 is partitioned from the substrate processing region 1033 by an ion suppressor 1023 and a showerhead 1025.

A top plate 1017, ion suppressor 1023, showerhead 1025, and a substrate support 1065 (also known as a pedestal), having a substrate 1055 disposed thereon, are shown and may each be included according to all embodiments described herein. The pedestal 1065 may have a heat exchange channel through which a heat exchange fluid flows to control the temperature of the substrate 1055. This configuration may allow the substrate 1055 temperature to be cooled or heated to maintain relatively low temperatures, such as between −20° C. to 200° C. The pedestal 1065 may also be resistively heated to relatively high temperatures, such as between 100° C. and 1100° C., using an embedded heater element.

The etchant precursors flow from the etchant supply system 1010 through the holes in the top plate 1017 into the remote plasma region 1015. The structural features may include the selection of dimensions and cross-sectional geometries of the apertures in the top plate 1017 to deactivate back-streaming plasma in cases where a plasma is generated in remote plasma region 1015. The top plate 1017, or a conductive top portion of the substrate processing chamber 1001, and the showerhead 1025 are shown with an intervening insulating ring 1020, which allows an AC potential to be applied to the top plate 1017 relative to the showerhead 1025 and/or the ion suppressor 1023. The insulating ring 1020 may be positioned between the top plate 1017 and the showerhead 1025 and/or the ion suppressor 1023 enabling a capacitively-coupled plasma (CCP) to be formed in the remote plasma region 1015. The remote plasma region 1015 houses the remote plasma.

The plurality of holes in the ion suppressor 1023 may be configured to control the passage of the activated gas, i.e., the ionic, radical, and/or neutral species, through the ion suppressor 1023. For example, the aspect ratio of the holes, or the hole diameter to length, and/or the geometry of the holes may be selected so that the flow of ionically-charged species in the activated gas passing through the ion suppressor 1023 is reduced. The holes in the ion suppressor 1023 may include a tapered portion that faces the remote plasma region 1015, and a cylindrical portion that faces the showerhead 1025. The cylindrical portion may be shaped and dimensioned to control the flow of ionic species passing to and through the showerhead 1025. An adjustable electrical bias may also be applied to the ion suppressor 1023 as an additional means to control the flow of ionic species through the suppressor. The ion suppressor 1023 may function to reduce or eliminate the amount of ionically charged species traveling from the plasma generation region to the substrate. Uncharged neutral and radical species may still pass through the openings in the ion suppressor to react with the substrate.

Remote plasma power can be of a variety of frequencies or a combination of multiple frequencies. The remote plasma may be provided by remote RF power delivered from the remote plasma power supply 1068 to the top plate 1017 relative to the ion suppressor 1023, relative to the showerhead 1025, or relative to both the ion suppressor 1023 and the showerhead 1025 (as shown). The remote RF power may be between 10 watts and 10,000 watts, between 10 watts and 5,000 watts, preferably between 25 watts and 2000 watts or more preferably between 50 watts and 1500 watts to increase the longevity of chamber components. The remote RF frequency applied in the exemplary processing system to the remote plasma region may be low RF frequencies less than 200 kHz, higher RF frequencies between 10 MHz and 15 MHz, or microwave frequencies greater than 1 GHz in embodiments. The plasma power may be capacitively-coupled (CCP) or inductively-coupled (ICP) into the remote plasma region.

Plasma effluents derived from the etchant precursors in the remote plasma region 1015 may travel through apertures in the ion suppressor 1023, and/or the showerhead 1025 and into the substrate processing region 1033 through throughholes or the first fluid channels 1019 of the showerhead in embodiments. Little or no plasma may be present in substrate processing region 1033 during the remote plasma etch process. The plasma effluents react with the substrate to etch material from the substrate.

The showerhead 1025 may be a dual channel showerhead (DCSH). The dual channel showerhead 1025 may provide for etching processes that allow for separation of etchants outside of the substrate processing region 1033 to provide limited interaction with chamber components and each other prior to being delivered into the substrate processing region 1033. The showerhead 1025 may comprise an upper plate 1014 and a lower plate 1016. The plates may be coupled with one another to define a volume 1018 between the plates. The plate configuration may provide the first fluid channels 1019 through the upper and lower plates, and the second fluid channels 1021 through the lower plate 1016. The formed channels may be configured to provide fluid access from the volume 1018 through the lower plate 1016 via the second fluid channels 1021 alone, and the first fluid channels 1019 may be fluidly isolated from the volume 1018 between the plates and the second fluid channels 1021. The volume 1018 may be fluidly accessible through a side of the showerhead 1025 and used to supply an unexcited precursor in embodiments.

Optionally, a bias plasma power may be present in the substrate processing region in embodiments. The bias plasma may be used to further excite plasma effluents already excited in the remote plasma. The bias plasma refers to a local plasma located just above the substrate. The term bias plasma is used since the plasma effluents may be ionized and/or accelerated towards the substrate to beneficially accelerate or provide incoming alignment to some etch processes. The bias plasma may be formed by applying bias plasma power from a bias plasma power supply 1069 to the substrate 1055/pedestal 1065 relative to the ion suppressor 1023, relative to the showerhead 1025, or relative to both the ion suppressor 1023 and the showerhead 1025 (as shown). The bias RF plasma power may be lower than the remote RF power. The bias RF plasma power may be below 20%, below 15%, below 10% or below 5% of the remote RF plasma power. The bias RF plasma power may be between 1 watt and 1,000 watts, between 1 watt and 500 watts, or between 2 watts and 100 watts in embodiments. The bias RF plasma frequency applied in the exemplary processing system to the remote plasma region may be low RF plasma frequencies less than 200 kHz, higher RF plasma frequencies between 10 MHz and 15 MHz, or microwave frequencies greater than 1 GHz in embodiments. The bias RF plasma frequency may be different from the remote RF frequency to further improve the integrity of the optical emission spectra. The plasma power may be capacitively-coupled (CCP) or inductively-coupled (ICP) into the substrate plasma region.

A viewport 1071 is disposed on the side of the substrate processing chamber 1001 and forms a border of the substrate processing region 1033. The viewport 1071 transmits optical radiation and may be transmissive in the infrared portion of the optical spectrum. Viewports described herein may be transmissive between 650 nm and 800 nm, between 680 nm and 760 nm or between 700 nm and 740 nm in embodiments. An optical emission spectrometer (OES) is disposed outside the viewport 1071 and configured to receive optical radiation, preferably infrared radiation, originating from the bias plasma formed in the substrate processing region 1033. In cases where there is no bias plasma, a weak plasma may be formed on the interior side of the viewport 1071 to facilitate the acquisition of the optical emission spectrum by the optical emission spectrometer. The characteristics of the weak plasma (power, frequency) may be the same as the bias power properties provided earlier, according to embodiments. For example, the weak RF plasma power may be below 20%, below 15%, below 10% or below 5% of the remote RF plasma power. The weak RF plasma power may be between 1 watt and 1,000 watts, between 1 watt and 500 watts, or between 2 watts and 100 watts in embodiments. The weak RF plasma frequency applied in the exemplary processing system to the remote plasma region may be low RF plasma frequencies less than 200 kHz, higher RF plasma frequencies between 10 MHz and 15 MHz, or microwave frequencies greater than 1 GHz in embodiments. The weak RF plasma frequency may be different from the remote RF frequency to further improve the integrity of the optical emission spectra. The weak plasma power may be capacitively-coupled (CCP) or inductively-coupled (ICP) into the substrate plasma region.

Figure 2:
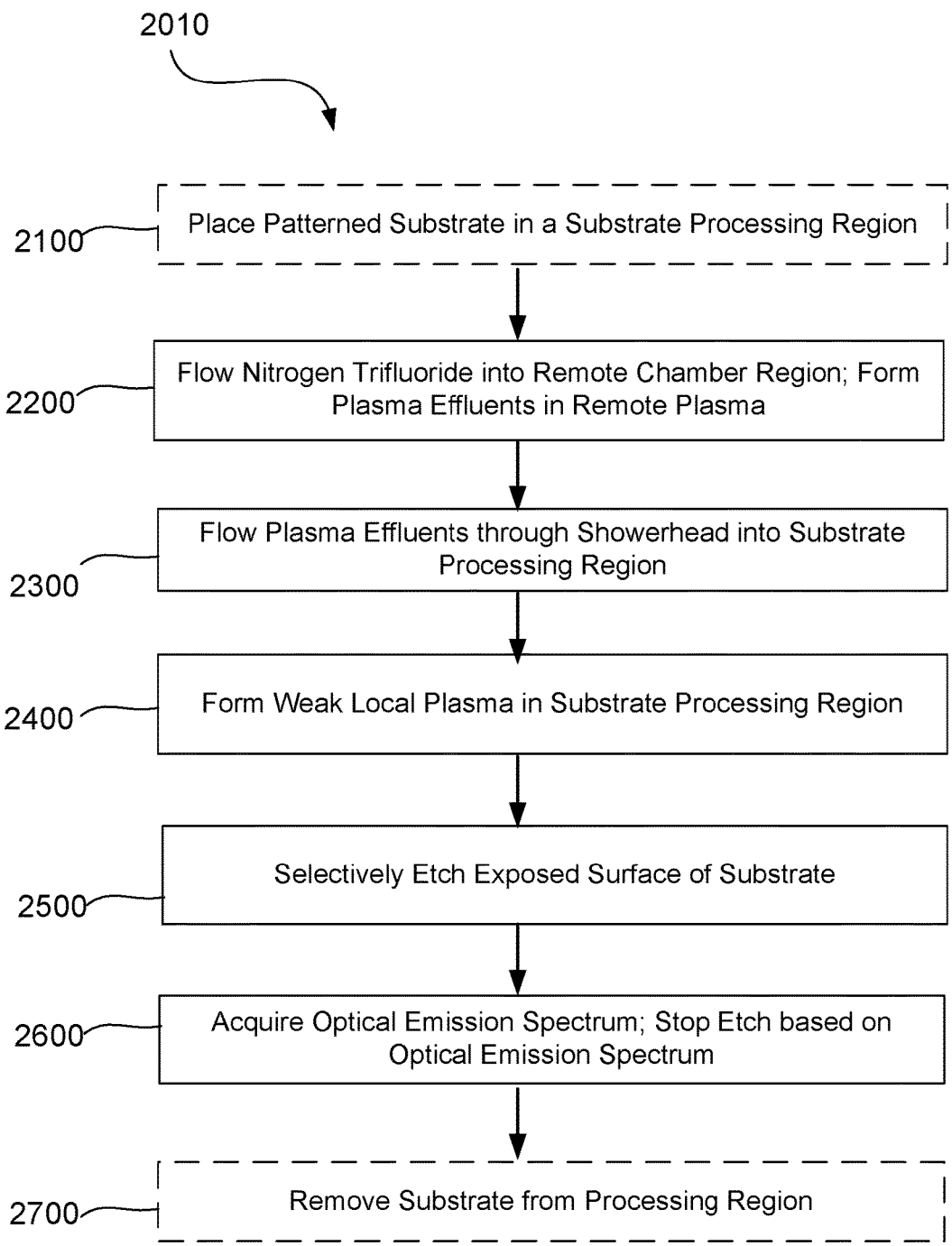
FIG. 2 is a flow chart of a remote plasma etch process according to embodiments.

To better understand and appreciate the embodiments disclosed herein, reference is now made to FIG. 2 which is a flow chart of a highly selective etch process 2010 according to embodiments. Prior to the first operation, the substrate is patterned and then placed within the substrate processing region in optional operation 2100. A fluorine-containing precursor (e.g. $NF_3$) may be flowed into the remote plasma region in operation 2200. A remote plasma is formed from the fluorine-containing precursor in the remote plasma region by applying a remote plasma power across the remote plasma region to form plasma effluents. The plasma effluents are flowed through a showerhead disposed between the remote plasma region and the substrate processing region in operation 2300. The plasma effluents flow through the showerhead from the remote plasma region into the substrate processing region. A bias plasma is formed by applying a bias plasma power across the substrate processing region to further excite the plasma effluents in operation 2400. The bias plasma power is less than the remote plasma power and the bias plasma may be referred to as a "weak" plasma in embodiments. Portions of a patterned substrate are selectively etched in operation 2500. An optical emission spectrum is acquired through a viewport in the side of the substrate processing chamber (operation 2600) and the etch is stopped based on the results. The viewport forms a border of the substrate processing region. Optionally, the patterned substrate is removed from the substrate processing region (operation 2700).

Figure 3A:
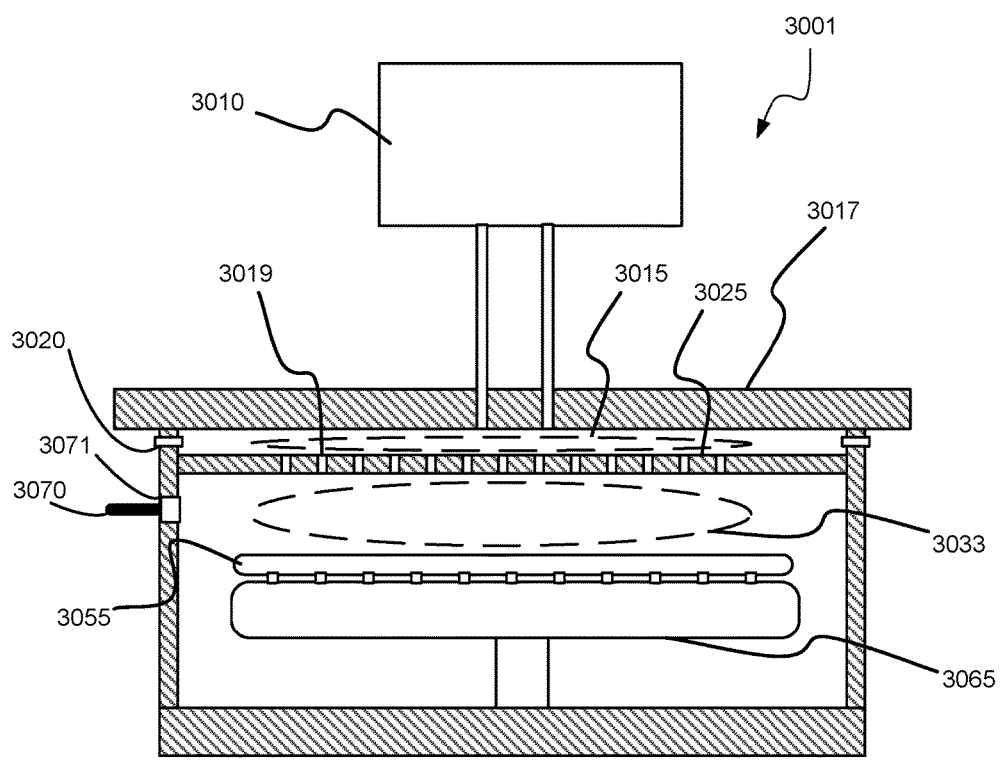
FIG. 3A shows a schematic cross-sectional view of a substrate processing chamber according to embodiments.

FIG. 3A shows a schematic cross-sectional view of an exemplary substrate processing chamber. Process and equipment parameters given earlier apply to all embodiments described herein. Similarly, process and equipment parameters given here and in subsequent discussions may be used for all other embodiments described herein. The substrate processing chamber 3001 has a remote plasma region 3015 and a substrate processing region 3033 inside. The remote plasma region 3015 is partitioned from the substrate processing region 3033 by a showerhead 3025 with through-holes 3019 configured to pass plasma effluents.

A top plate 3017, showerhead 3025, and a pedestal 3065 supporting a substrate 3055 are shown. A fluorine-containing precursor may flow from the etchant supply system 3010 into the remote plasma region 3015. The top plate 3017 and the showerhead 3025 are electrically-separated conductors separated by insulating ring 3020. An AC potential (the remote plasma power) is applied to the top plate 3017 relative to the showerhead 3025 to form the remote plasma. The remote plasma may be a capacitively-coupled plasma (CCP) in the remote plasma region 3015. Plasma frequencies and plasma powers provided by a remote plasma power supply (not shown) were provided previously.

Plasma effluents derived from the fluorine precursors in the remote plasma region 3015 may travel through the through-holes 3019 in the showerhead 3025 and into the substrate processing region 3033. A bias plasma power is applied by a bias plasma power supply (not shown) to the substrate processing region 3033. The bias plasma further excites the plasma effluents. The bias plasma weakly ionizes and accelerates plasma effluents towards the substrate to beneficially accelerate or provide incoming alignment to the etch processes. The bias plasma may be formed by applying bias plasma power from a bias plasma power supply to the substrate 3055/pedestal 3065 relative to the showerhead 3025. The plasma effluents react with the substrate to etch material from the substrate.

Acquisition of optical emission spectra uses the recombination of electrons with ions to emit photons indicative of a presence of specific atomic species. In the embodiment represented in FIG. 3A, the bias plasma is sufficient to supply the ionization needed to acquire an optical emission spectrum. To further enable the measurement, a viewport 3071 is disposed in the side of the substrate processing chamber 3001. The optical emission spectrum is measured using an optical emission spectrometer on the outside of the viewport 3071.

Figure 3B:
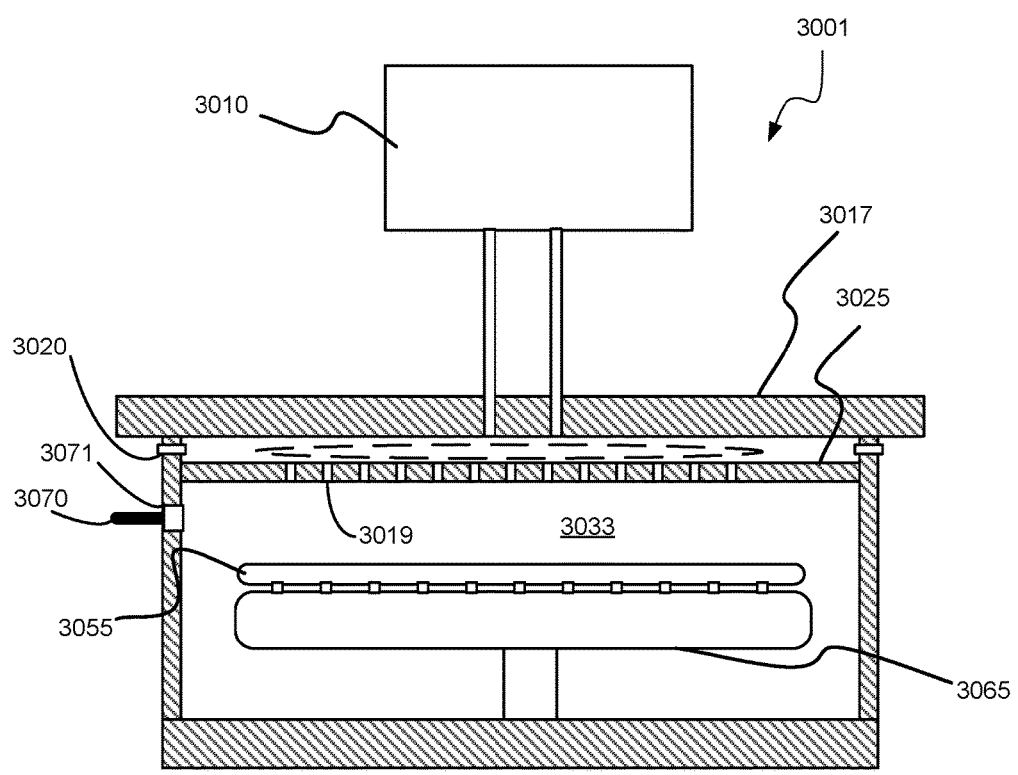
FIG. 3B shows a schematic cross-sectional view of a substrate processing chamber according to embodiments.

FIG. 3B shows a schematic cross-sectional view of an exemplary substrate processing chamber. The substrate processing chamber 3001 has a remote plasma region 3015 and a substrate processing region 3033 inside. The remote plasma region 3015 is partitioned from the substrate processing region 3033 by a showerhead 3025 with through-holes 3019 to pass plasma effluents. A top plate 3017, showerhead 3025, and a pedestal 3065 supporting a substrate 3055 are shown. A fluorine-containing precursor may flow from the etchant supply system 3010 into the remote plasma region 3015. An AC potential (the remote plasma power) is applied to the top plate 3017 relative to the showerhead 3025 to form the remote plasma.

Plasma effluents derived from the fluorine precursors in the remote plasma region 3015 travel through the through-holes 3019 in the showerhead 3025 and into the substrate processing region 3033. The plasma effluents react with the substrate to etch material from the substrate.

No bias plasma power is applied to the substrate processing region 3033 in embodiments. The substrate processing region 3033 may be referred to as plasma-free and may be devoid of plasma in embodiments. A weak plasma near the substrate processing region is used to obtain an optical emission spectrum. The weak plasma results in recombination of electrons with ions and concomitant emission of photons indicative of a presence of specific atomic species. Therefore a weak plasma is formed just on the inside of a viewport 3071 by a variety of techniques to be described herein. The viewport 3071 is disposed in the side of the substrate processing chamber 3001. The optical emission spectrum is measured using an optical emission spectrometer on the outside of the viewport 3071. The weak plasma is formed by applying weak plasma power from a weak plasma power supply to one or more electrode(s) (not shown) near the viewport 3071. The weak RF plasma power may be lower than the remote RF power. A relatively low weak RF plasma power avoids swamping the remote plasma OES signal with characteristics of the weak local plasma. The weak RF plasma power may be below 10%, below 8%, below 5% or below 3% of the remote RF plasma power. The weak RF plasma power may be between 0.1 watts and 300 watts, between 0.2 watts and 100 watts, or between 0.5 watts and 20 watts in embodiments. The weak RF plasma frequency applied in the exemplary processing system to the remote plasma region may be low RF plasma frequencies less than 200 kHz, higher RF plasma frequencies between 10 MHz and 15 MHz, or microwave frequencies greater than 1 GHz in embodiments. The weak RF plasma frequency may be different from the remote RF frequency to further improve the integrity of the optical emission spectra. For example, the weak RF plasma frequency may be 60 kHz and the remote RF frequency may be 13 MHz. The plasma power may be capacitively-coupled (CCP) or inductively-coupled (ICP) into the substrate plasma region.

The pressure in the substrate processing region and the remote plasma region during the etching operations may be between 0.01 Torr and 50 Torr, between 0.1 Torr and 15 Torr or between 0.5 Torr and 10 Torr in embodiments. The temperature of the patterned substrate during the etching operations may be between −20° C. and 450° C., between 0° C. and 350° C. or between 5° C. and 200° C. in embodiments.

Figure 4:
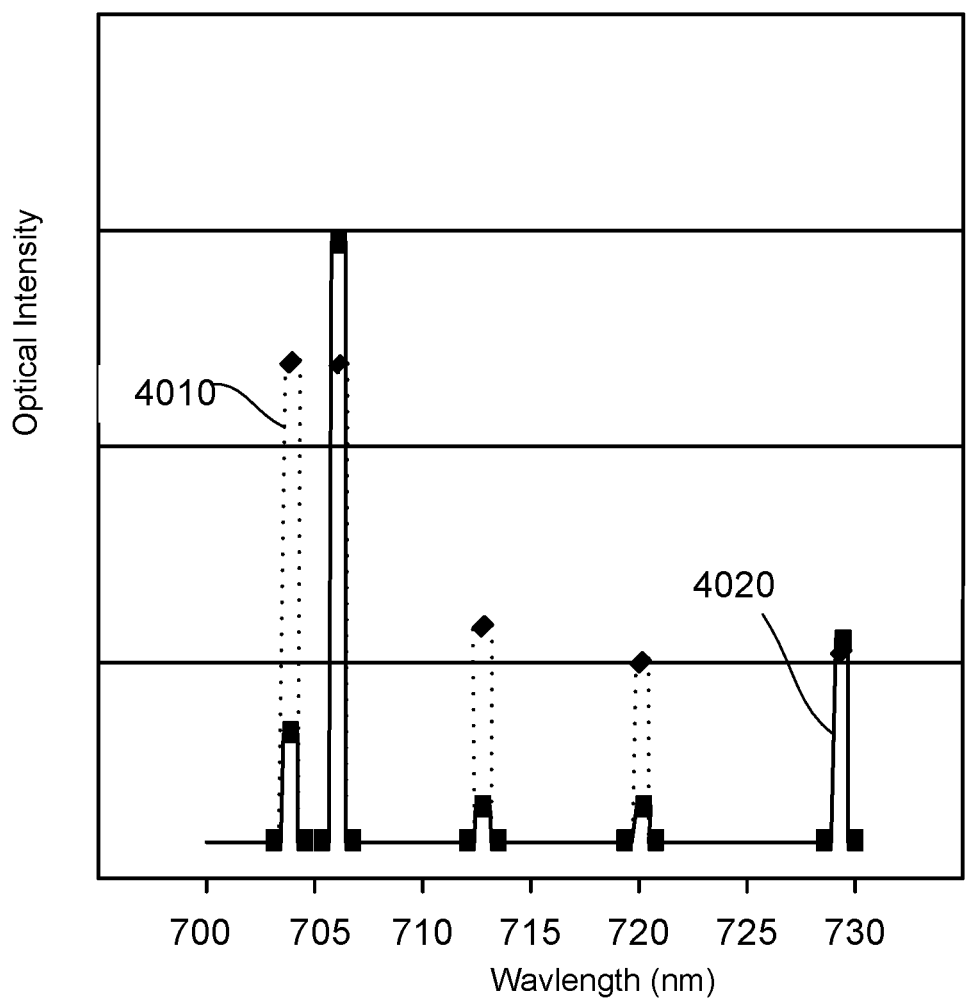
FIG. 4 is an optical emission spectrum according to embodiments.

Reference is now made to FIG. 4 which is plot of an optical emission spectra. An optical emission spectrum 4010 is depicted which represents a concurrent remote plasma and a weak local plasma. Another optical emission spectrum 4020 is depicted which represents only a weak local plasma. The peaks near 703.7 nm, 712.8 nm, and 720.2 nm correspond with fluorine atom concentration. The peaks near 706.5 nm and 728.1 nm correspond with helium atom concentration. Helium or another inert gas may be used to benefit the etch process but may also be useful to compare and normalize the fluorine peaks. Qualitatively, the fluorine measurements can be seen to become more pronounced when the remote plasma is in use. More generally, the fluorine measurements may be used to determine whether the fluorine concentration is changing, has reached a plateau, or has reached a predetermined setpoint during an etch process.

Figure 5:
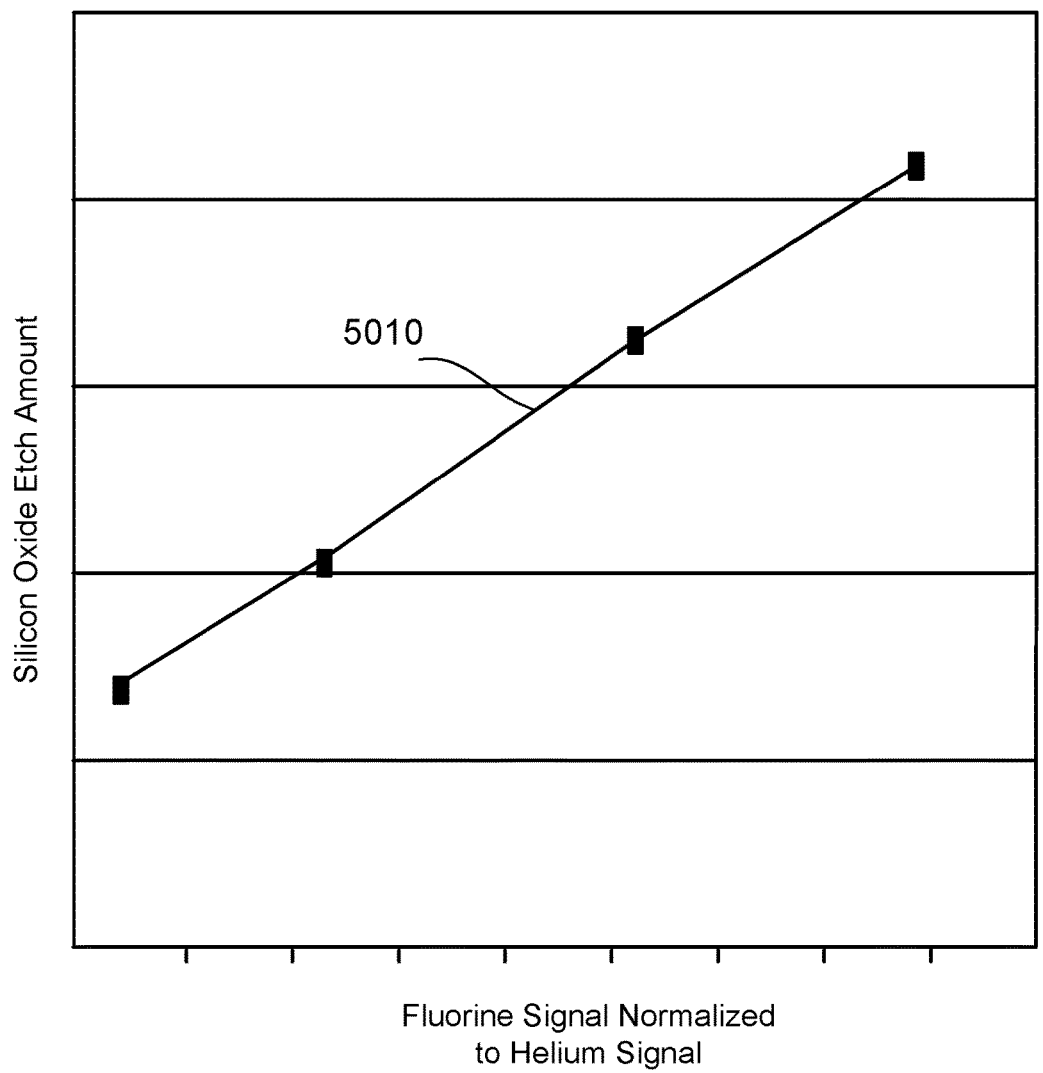
FIG. 5 is a plot of etch amount correlation with fluorine signal according to embodiments.

FIG. 5 is a plot of etch amount correlation with fluorine signal according to embodiments. The fluorine signal normalized to helium signal is shown on the x-axis whereas the etch amount corresponds to the y-axis. A plot of etch amount (proportion to etch rate) versus normalized fluorine signal 5010 is shown to be roughly linear with an offset. The linearity enables the normalized fluorine signal to be an in-situ indicator of the etch rate of a substrate without measuring the substrate directly.

Figure 6A:
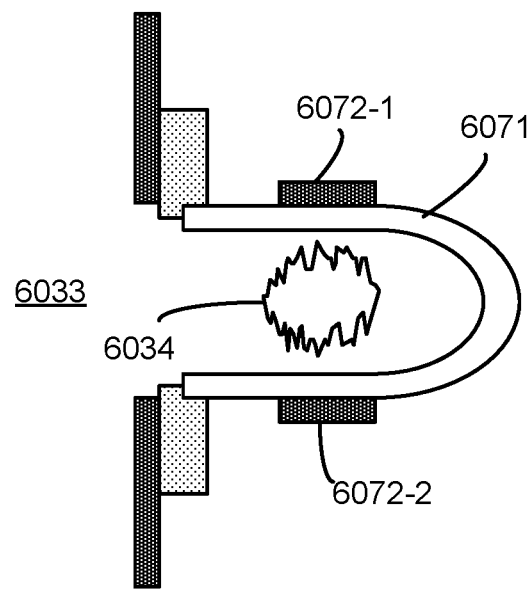
FIG. 6A shows a cross-sectional side view of a weak plasma viewport according to embodiments.
Figure 6B:
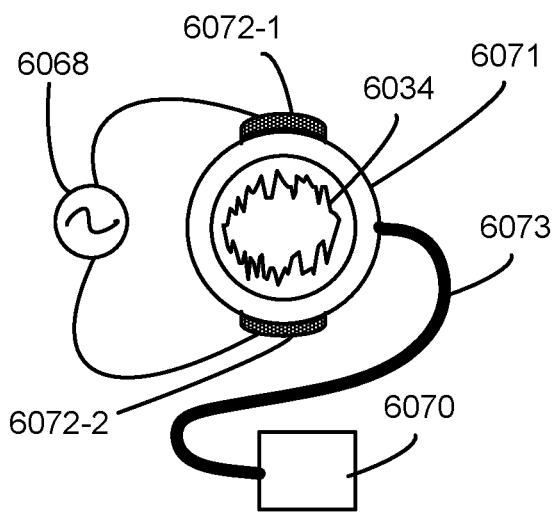
FIG. 6B shows a cross-sectional end view of a weak plasma viewport according to embodiments.

FIGS. 6A and 6B show cross-sectional side views of a weak plasma viewport according to embodiments. FIG. 6A shows a substrate processing region 6033 with a tubular viewport 6071 affixed to the side and forming a vacuum seal with the wall of the substrate processing chamber. A first electrode 6072-1 and a second electrode 6072-2 are affixed to the tubular viewport 6071 on opposite sides. All electrodes described herein may be copper adhesive tape or silver paste to facilitate attaching the electrodes to the various viewports according to embodiments. Other adhesive formats may also be used. Alternatively, the electrodes may simply be placed near the tubular viewport 6071 on opposite sides since mechanical contact between the viewport and the electrodes is not necessary to form the plasma. A weak plasma 6034 is formed on the inside of the tubular viewport 6071 by applying a weak RF plasma power from a weak RF plasma power supply (not shown) between the first electrode 6072-1 and the second electrode 6072-2. FIG. 6B shows an end view of the same configuration and includes a view of the weak plasma power supply 6068. A fiber optic cable 6073 is configured to guide optical radiation from the weak plasma 6034 through the tubular viewport 6071 and into the optical emission spectrometer 6070.

FIGS. 7A, 7B, and 7C show cross-sectional side views of a weak plasma viewport according to embodiments. FIG. 7A shows a substrate processing region 7033 with a tubular viewport 7071 affixed to the side and forming a vacuum seal with the wall of the substrate processing chamber. An electrode 7072-1 is affixed to the tubular viewport 7071 around the exterior of the tubular viewport 7071. The electrode 7072-1 may be a piece of conducting adhesive tape (e.g. copper) or a layer of conductive paste (e.g. silver) to facilitate attaching the electrode 7072-1 to the tubular viewport 7071 according to embodiments. The electrode 7072-1 may simply be a conducting hoop looped loosely around the tubular viewport 7071 since forming the weak plasma does not rely on mechanical contact between the tubular viewport 7071 and the electrode 7072-1. A weak plasma 7034-1 is formed on the inside of the tubular viewport 7071 by applying a weak RF plasma power from a weak RF plasma power supply 7068-1 between the electrode 7072-1 and the rest of the substrate processing chamber or the wall shown as a border of the substrate processing region 7033. Also shown is a fiber optic cable 7073 configured to guide optical radiation from the weak plasma 7034 through the tubular viewport 7071 and into the optical emission spectrometer 7070. FIG. 7B shows an end view of the same configuration and includes a view of the electrode 7072-1 which is shaped like a hoop. FIG. 7C shows a related configuration having an electrode 7072-2 over the end of the tubular viewport 7071 and the fiber optic cable 7073 is relocated to peer at the weak plasma 7034-2 from a different angle through an unobstructed portion of the tubular viewport 7071. A weak RF plasma power supply 7068-2 provides the weak RF plasma power between the electrode 7072-2 and the wall of the substrate processing chamber.

Figure 8A:
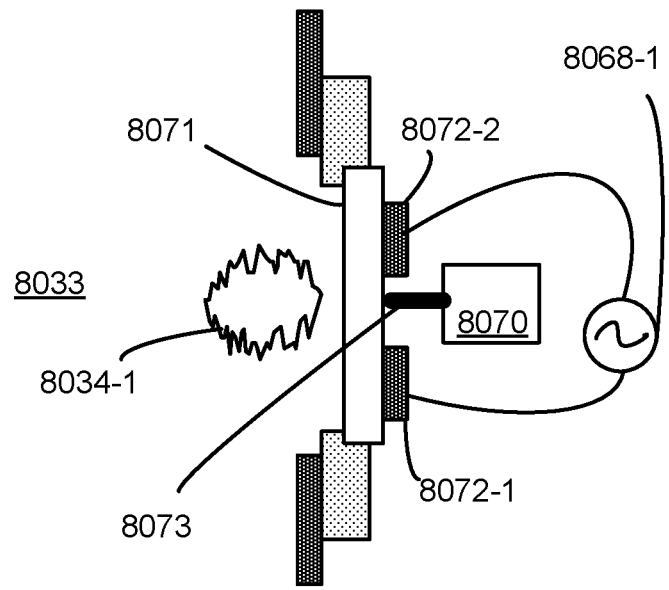
FIG. 8A shows a cross-sectional side view of a weak plasma viewport according to embodiments.
Figure 8B:
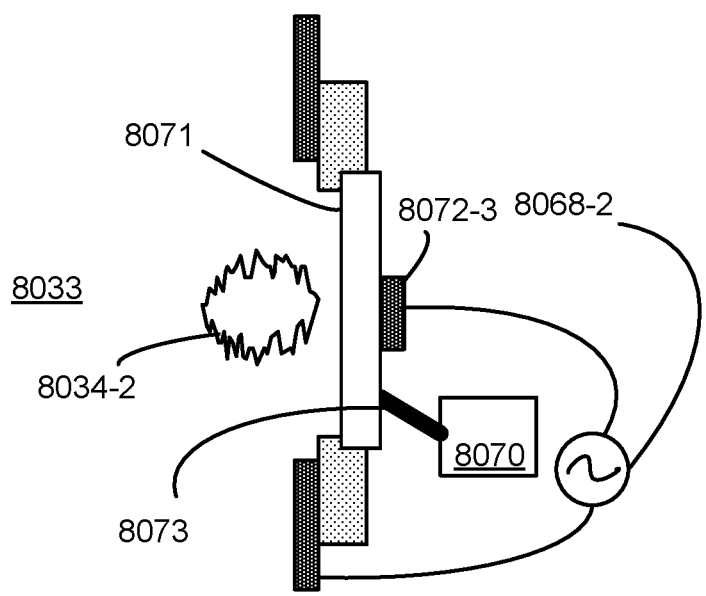
FIG. 8B shows a cross-sectional side view of a weak plasma viewport according to embodiments.

FIGS. 8A and 8B show cross-sectional side views of a weak plasma viewport according to embodiments. FIG. 8A shows a substrate processing region 8033 with a planar viewport 8071 affixed to the side and forming a vacuum seal with the wall of the substrate processing chamber. A first electrode 8072-1 and a second electrode 8072-2 are affixed to the planar viewport 8071 without any direct electrical connection between them. The first electrode 8072-1 and the second electrode may be pieces of conducting adhesive tape (e.g. copper), a layer of conductive paste (e.g. silver) or electrodes placed near or adjacent to the planar viewport 8071. The electrodes (8072-1, 8072-2) do not need to be in mechanical contact with the planar viewport 8071, in embodiments, to provide the capability of forming a weak plasma 8034-1. The weak plasma 8034-1 is formed on the inside of the planar viewport 8071 by applying a weak RF plasma power from a weak RF plasma power supply 8068-1 between the first electrode 8072-1 and the second electrode 8072-2. Also shown is a fiber optic cable 8073 configured to guide optical radiation from the weak plasma 8034-1 through the planar viewport 8071 and into the optical emission spectrometer 8070. FIG. 8B shows a substrate processing region 8033 with a planar viewport 8071 affixed to the side and forming a vacuum seal with the wall of the substrate processing chamber. An electrode 8072-3 is affixed to the planar viewport 8071. The first electrode 8072-1 may again be a piece of conducting adhesive tape, a layer of conductive paste, or an electrode placed very near or contacting the planar viewport 8071. The weak plasma 8034-1 is formed on the inside of the planar viewport 8071 by applying a weak RF plasma power from a weak RF plasma power supply 8068-2 between the electrode 8072-3 and the rest of the substrate processing chamber or the wall shown as a border of the substrate processing region 8033. Also shown is a fiber optic cable 8073 configured to guide optical radiation from the weak plasma 8034-2 through the planar viewport 8071 and into the optical emission spectrometer 8070.

The tubular viewports described herein may be more prone to breakage since they stick out from the substrate processing chamber. The planar viewports provide the benefit of reducing the chance of accidentally breaking the viewport. The thickness of the planar viewports described herein affect the intensity of the weak plasmas inside the substrate processing chamber near the substrate. The thickness of the planar viewports may be between 1 mm and 15 mm, between 2 mm and 10 mm or preferably between 3 mm and 8 mm according to embodiments. The height and/or width of the planar viewports (as viewed from the axis of the thinnest dimension) may be between 20 mm and 100 mm or between 30 mm and 70 mm in embodiments. The fiber optic cable in all embodiments described herein may be positioned to the side of the substrate and just above the major plane of the substrate to preferentially sample the portion of the plasma effluents most likely to be participating in the etch process. The fiber optic cable may point horizontally (parallel to the major plane of the substrate) between 1 mm and 10 mm above the top surface of the substrate according to embodiments.

In embodiments, an ion suppressor (which may be the showerhead) may be used to provide radical and/or neutral species for gas-phase etching. The ion suppressor may also be referred to as an ion suppression element and may be positioned between the remote chamber region and the substrate processing region along with the showerhead. In embodiments, for example, the ion suppressor is used to filter etching plasma effluents en route from the remote plasma region(s) to the substrate processing region. The ion suppressor may be used to provide a reactive gas having a higher concentration of radicals than ions. Plasma effluents pass through the ion suppressor disposed between the remote plasma region and the substrate processing region. The ion suppressor functions to dramatically reduce or substantially eliminate ionic species traveling from the plasma generation region to the substrate. The ion suppressors described herein are simply one way to achieve a low electron temperature in the substrate processing region during the gas-phase etch processes described herein.

In embodiments, an electron beam is passed through the substrate processing region in a plane parallel to the substrate to reduce the electron temperature of the plasma effluents. A simpler showerhead may be used if an electron beam is applied in this manner. The electron beam may be passed as a laminar sheet disposed above the substrate in embodiments. The electron beam provides a source of neutralizing negative charge and provides a more active means for reducing the flow of positively charged ions towards the substrate and increasing the etch selectivity in embodiments. The flow of plasma effluents and various parameters governing the operation of the electron beam may be adjusted to lower the electron temperature measured in the substrate processing region.

The electron temperature may be measured using a Langmuir probe in the substrate processing region during excitation of a plasma in the remote plasma. In all plasma-free regions described herein (especially in the substrate processing region), the electron temperature may be less than 0.5 eV, less than 0.45 eV, less than 0.4 eV, or less than 0.35 eV. These extremely low values for the electron temperature are enabled by the presence of the electron beam, showerhead and/or the ion suppressor. Uncharged neutral and radical species may pass through the electron beam and/or the openings in the ion suppressor to react at the substrate. Such a process using radicals and other neutral species can reduce plasma damage compared to conventional plasma etch processes that include sputtering and bombardment. Embodiments disclosed herein are also advantageous over conventional wet etch processes where surface tension of liquids can cause bending and peeling of small features.

The substrate processing region may be described herein as "plasma-free" during the etch processes described herein. "Plasma-free" does not necessarily mean the region is devoid of plasma. A weak plasma may be present to perform the optical emission spectroscopy measurement but the region directly above the substrate may be devoid of plasma since the weak plasma is positioned off to the side of the substrate processing region in embodiments. Ionized species and free electrons created within the plasma region may travel through pores (apertures) in the partition (showerhead) at exceedingly small concentrations. The borders of the plasma in the remote plasma region (e.g. the remote chamber region and/or the remote plasma region) may encroach to some small degree upon the substrate processing region through the apertures in the showerhead. Furthermore, a low intensity plasma may be created in the substrate processing region without eliminating desirable features of the etch processes described herein. All causes for a plasma having much lower intensity ion density than the remote plasma region during the creation of the excited plasma effluents do not deviate from the scope of "plasma-free" as used herein.

As used herein "substrate" may be a support substrate with or without layers formed thereon. The patterned substrate may be an insulator or a semiconductor of a variety of doping concentrations and profiles and may, for example, be a semiconductor substrate of the type used in the manufacture of integrated circuits. Exposed "silicon oxide" of the patterned substrate is predominantly $SiO_2$ but may include concentrations of other elemental constituents such as, e.g., nitrogen, hydrogen and carbon. In some embodiments, silicon oxide portions etched using the methods disclosed herein consist essentially of silicon and oxygen. Exposed "silicon nitride" of the patterned substrate is predominantly $Si_3N_4$ but may include concentrations of other elemental constituents such as, e.g., oxygen, hydrogen and carbon. In some embodiments, silicon nitride portions described herein consist essentially of silicon and nitrogen. Generally speaking, a first exposed portion of a patterned substrate is etched faster than a second exposed portion. The first exposed portion may have an atomic stoichiometry which differs from the second exposed portion. In embodiments, the first exposed portion may contain an element which is not present in the second exposed portion. Similarly, the second exposed portion may contain an element which is not present in the first exposed portion according to embodiments.

The term "precursor" is used to refer to any chemical which takes part in a reaction to either remove material from or deposit material onto a surface. "Plasma effluents" describe gas exiting from the remote plasma region and entering the remote chamber region and/or the substrate processing region. Plasma effluents are in an "excited state" wherein at least some of the gas molecules are in vibrationally-excited, dissociated and/or ionized states. A "radical precursor" is used to describe plasma effluents (a gas in an excited state which is exiting a plasma) which participate in a reaction to either remove material from or deposit material on a surface. "Radical-fluorine precursors" describe radical precursors which contain fluorine but may contain other elemental constituents. The phrase "inert gas" refers to any gas which does not form chemical bonds when etching or being incorporated into a film. Exemplary inert gases include noble gases but may include other gases so long as no chemical bonds are formed when (typically) trace amounts are trapped in a film.

Having disclosed several embodiments, it will be recognized by those of skill in the art that various modifications, alternative constructions, and equivalents may be used without departing from the spirit of the disclosed embodiments. Additionally, a number of well-known processes and elements have not been described to avoid unnecessarily obscuring the present embodiments. Accordingly, the above description should not be taken as limiting the scope of the claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the claims, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the dielectric material" includes reference to one or more dielectric materials and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

The invention claimed is:

1. A method of etching a substrate, the method comprising:
   placing the substrate in a substrate processing region of a substrate processing chamber;
   flowing a fluorine-containing precursor into a remote plasma region separated from the substrate processing region by a showerhead;
   forming a remote plasma having a remote plasma power in the remote plasma region;
   producing plasma effluents from the fluorine-containing precursor in the remote plasma in the remote plasma region;
   flowing the plasma effluents through the showerhead into the substrate processing region;
   etching the substrate with the plasma effluents;
   forming a local plasma having a local plasma power in the substrate processing region while maintaining the remote plasma and etching the substrate, wherein the remote plasma power of the remote plasma exceeds the local plasma power of the local plasma by a factor of ten or more;
   acquiring an optical emission spectrum through a viewport affixed to a side of the substrate processing chamber and forming a border of the substrate processing region, wherein the optical emission spectrum represents intensity as a function of optical wavelength, and wherein the optical emission spectrum is acquired with an optical emission spectrometer;
   determining a fluorine signal from the optical emission spectrum; and
   determining an etch rate of the substrate based on the fluorine signal, wherein the fluorine signal is linearly correlated with the etch rate of the substrate.

2. The method of claim 1, wherein the local plasma is centered over the substrate.

3. The method of claim 1, wherein the local plasma is disposed above the substrate and outside an edge of the substrate near the viewport.

4. The method of claim 3, wherein the local plasma is formed using an electrode that is different from electrodes used for forming the remote plasma and that is disposed on the outside of the viewport, and wherein the local plasma power is applied between the electrode and the substrate processing chamber.

5. The method of claim 3, wherein the local plasma is formed using a first electrode and a second electrode that are different from electrodes used for forming the remote plasma, wherein the first electrode and the second electrode are each disposed on the outside of the viewport, and wherein the local plasma power is applied between the first electrode and the second electrode.

6. The method of claim 1, wherein the local plasma is formed outside a radial edge of the substrate and proximate the viewport, and wherein a region that is within the substrate processing region and above the substrate is plasma free.

7. The method of claim 1, further comprising etching the substrate with the local plasma, wherein the local plasma is a bias plasma.

8. A method of etching a substrate, the method comprising:
   placing the substrate in a substrate processing region of a substrate processing chamber;
   flowing a fluorine-containing precursor into a remote plasma region separated from the substrate processing region by a showerhead;
   forming a remote plasma having a remote plasma power in the remote plasma region;
   producing plasma effluents from the fluorine-containing precursor in the remote plasma in the remote plasma region;

flowing the plasma effluents through the showerhead into the substrate processing region;

etching the substrate with the plasma effluents, wherein an electron temperature within the substrate processing region is less than 0.5 eV while etching the substrate;

forming a local plasma having a local plasma power in the substrate processing region while maintaining the remote plasma and etching the substrate, wherein the remote plasma power of the remote plasma exceeds the local plasma power of the local plasma by a factor of ten or more;

acquiring an optical emission spectrum through a viewport affixed to a side of the substrate processing chamber and forming a border of the substrate processing region, wherein the optical emission spectrum represents intensity as a function of optical wavelength and the optical emission spectrum is acquired with an optical emission spectrometer;

determining at least one signal from the optical emission spectrum; and determining an etch rate of the substrate based on the at least one signal, wherein the at least one signal is linearly correlated with the etch rate of the substrate.

9. The method of claim 8, wherein a pressure in the substrate processing region and in the remote plasma region while etching the substrate is between 0.01 Torr and 50 Torr.

10. The method of claim 8, wherein a temperature of the substrate while etching the substrate is between −20° C. and 450° C.

11. The method of claim 8, wherein the at least one signal comprises a fluorine signal from the optical emission spectrum.

12. The method of claim 8, wherein the at least one signal comprises a fluorine signal representing a concentration of excited fluorine from both the remote plasma and the local plasma.

13. The method of claim 8, further comprising passing an electron beam above the substrate.

14. The method of claim 8, further comprising passing an electron beam as a laminar sheet above the substrate.

15. A method of etching a substrate, the method comprising:

flowing a fluorine-containing precursor into a remote plasma region of a substrate processing chamber;

forming a remote plasma having a remote plasma power in the remote plasma region to produce plasma effluents;

flowing the plasma effluents into a substrate processing region separated from the remote plasma region by a showerhead, wherein the substrate is housed in the substrate processing region;

etching the substrate with the plasma effluents;

forming a local plasma having a local plasma power in the substrate processing region while maintaining the remote plasma and etching the substrate, wherein the local plasma is formed outside a radial edge of the substrate and proximate a viewport affixed to a side of the substrate processing chamber and forming a border of the substrate processing region, wherein a region that is within the substrate processing region and above the substrate is plasma free;

acquiring an optical emission spectrum through the viewport;

determining at least one signal from the optical emission spectrum; and determining an etch rate of the substrate based on the at least one signal, wherein the at least one signal is linearly correlated with the etch rate of the substrate.

16. The method of claim 15, wherein the remote plasma power of the remote plasma exceeds the local plasma power of the local plasma by a factor of ten or more.

17. The method of claim 15, wherein the at least one signal comprises a fluorine signal.

18. The method of claim 15, further comprising passing an electron beam as a laminar sheet above the substrate in the substrate processing region, and wherein an electron temperature within the substrate processing region is less than 0.5 eV while etching the substrate.

* * * * *